(12) United States Patent
Anelli et al.

(10) Patent No.: US 6,458,337 B1
(45) Date of Patent: Oct. 1, 2002

(54) DIAGNOSTIC IMAGING CONTRAST AGENT WITH IMPROVED IN SERUM RELAXIVITY

(75) Inventors: Pier Lucio Anelli; Marco Lolli; Franco Fedeli; Mario Virtuani; Marino Brocchetta; Pierfrancesco Morosini; Daniela Palano, all of Milan (IT)

(73) Assignee: Dibra S.p.A, Milan (IT)

( * ) Notice: Subject to any disclaimer, the term of this patent is extended or adjusted under 35 U.S.C. 154(b) by 0 days.

(21) Appl. No.: 09/620,594

(22) Filed: Jul. 20, 2000

Related U.S. Application Data

(63) Continuation-in-part of application No. 08/904,685, filed on Aug. 1, 1997, now abandoned.

(30) Foreign Application Priority Data

Aug. 2, 1996 (IT) .......................... MI96A1685

(51) Int. Cl.[7] .............................. A61B 5/055
(52) U.S. Cl. .................... 424/9.36; 424/1.11; 424/1.65; 424/9.1; 424/9.3
(58) Field of Search .............................. 424/1.11, 1.65, 424/9.1, 9.3, 9.35, 9.36; 534/7, 10–16; 568/579

(56) References Cited

U.S. PATENT DOCUMENTS

| | | |
|---|---|---|
| 4,505,956 A | 3/1985 | Yamamoto et al. |
| 5,057,302 A | 10/1991 | Johnson et al. |
| 5,182,370 A | 1/1993 | Felder et al. |
| 5,453,264 A | 9/1995 | Mori et al. |
| 5,514,810 A | 5/1996 | Platzek et al. |
| 5,547,817 A | 8/1996 | Okada et al. |
| 5,567,411 A | 10/1996 | Keana et al. |
| 5,582,814 A | 12/1996 | Scott et al. |
| 5,672,335 A | 9/1997 | Krause et al. |
| 5,676,926 A | 10/1997 | Platzek et al. |
| 5,733,522 A | 3/1998 | Schmitt-Willich et al. |
| 5,746,995 A | 5/1998 | Maier |

FOREIGN PATENT DOCUMENTS

| | | |
|---|---|---|
| CA | 2177977 | 6/1995 |
| DE | 43 41 724 A | 6/1995 |
| WO | 96/16677 | 11/1995 |

*Primary Examiner*—Dameron L. Jones
(74) *Attorney, Agent, or Firm*—Nixon & Vanderhye P.C.

(57) ABSTRACT

Compounds of the formula

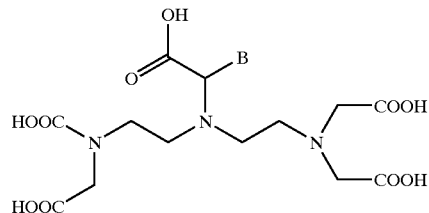

when chelated with metals exhibit improved serum relaxivity and are used in magnetic resonance imaging, particularly for imaging the blood pool.

8 Claims, No Drawings

DIAGNOSTIC IMAGING CONTRAST AGENT WITH IMPROVED IN SERUM RELAXIVITY

This application is a continuation-in-part of application Ser. No. 08/904,685, filed Aug. 1, 1997 now abandoned, the entire content of which is hereby incorporated by reference in this application.

TECHNICAL FIELD OF THE INVENTION

This invention relates to the Magnetic Resonance Imaging (M.R.I.), a technique used in the medical diagnosis field for a number of years, to rapidly detect a series of anomalies and/or pathological conditions of living human or animal body organs or tissues. (i. e.: Stark D. D., Bradley W. G. Jr., Eds.: "Magnetic Resonance Imaging", the C.V. Mosby Company, St. Louis, Mo. (USA), 1988). In particular, the invention relates to new chelating agents, especially aminopolycarboxylic acid derivative compounds and to metal chelates thereof with bivalent or trivalent paramagnetic ions and/or salts thereof as well as their use as M.R.I. contrast agents.

BACKGROUND OF THE INVENTION

Diagnostic imaging techniques, such as Magnetic Resonance Imaging have been used in medical diagnosis for a long time. The use of contrast media to improve tissue differentiation, to delineate structures or monitor physiological functions constitutes in some cases a fundamental contribution in the best formulation of some medical diagnosis and a valid support for radiologist work.

The medical use of aminopolycarboxylic acid or carboxylic acid derivatives and metal chelates thereof as M.R.I. contrast agents is well known. Said contrast agents, to simplify, can be seen as pertaining to two main groups: the linear and the cyclic ones.

The present invention relates to linear polyaminopolycarboxylic acid derivatives, as well as their complexes with paramagnetic metal ions, in particular the $Gd^{3+}$ ion.

Patent literature is rich in patent and patent applications relating to the use of linear polyaminopolycarboxylic acid derivatives in the preparation of MRI contrast agents. These compounds generally are derived from the simplest one, N,N,N',N",N"-diethylenetriamine-pentaacetic acid, (DTPA), of which the Meglumine salt of the $Gd^{3+}$ complex has been commercialised for a number of years as MAG-NEVIST®. To improve stability, water solubility and selectivity and to reduce toxicity of these contrast agents generally patent literature proposes the preparation of esters or amido derivatives of said acids or the introduction of substituents on the diethylene unit of the diethylenetriamine DTPA skeleton. As an example of said patent literature we can cite: Guerbet EP 661279; Concat Ltd., WO 95/05118; Dibra WO 95/15319; Mallinckrodt WO 94/08630; Green Gross Corp. JP 06016606 and JP 05229998; Mallinckrodt U.S. Pat. No. 5,141,740 and U.S. Pat. No. 5,077,037; Cockbain-Nycomed WO 91/15467 and WO 92/11232; Salutar U.S. Pat. Nos. 4,889,931 and 4,858,451; Abbot Laboratoires EP 279307; Nycomed EP 299795; Metasyn Inc. WO 95/28179; Schering EP 680 464; and document cited in these patent publications. Some documents further exist in which substituents have been introduced in à to one or more carboxylic DTPA groups; for example: Bracco EP-B-230893 and U.S. Pat. No. 5,182,370; Schering WO 96/16928, WO 96/16929, WO 96/26180 and DE 4341724 enclosing à derivatives, generally comprising an aromatic group, particularly useful for the imaging of the hepatobiliary system. In particular, some patent literature further exist, in which the introduction of an aromatic or lipophilic group on the chelant structure is specifically stated to make the contrast agent particularly useful for a best definition of the liver and the biliary duct: the General Hospital Corporation U.S. Pat. No. 4,899,755 and WO-A-86/06605.

Among the other relevant documents disclosing large substituents on a DTPA like skeleton, in particular on the at position to the carboxy groups of DTPA, the following can also be mentioned. U.S. Pat. No. 5,746,995 describes chelates compounds in which the DTPA skeleton is substituted on the α position of one of the carboxy residues of the terminal/lateral part of the molecule. Said substituents are lipophilic radicals that render the claimed compounds particularly useful for the imaging of liver, gallbladder and bile ducts. U.S. Pat. No. 5,672,335 discloses substituted DTPA derivatives, which carry substituents that render the same sufficiently lipophilic to be useful for the imaging of liver and the biliary tracts. These compounds are specific hepatobiliary contrast agents for X-ray imaging (computer tomography). U.S. Pat. No. 5,514,810 discloses a process for preparing complexses substituted in the α position of the central carboxylic acid of the molecule. Said compounds are in any case lipophilic tetraesters of the four terminal carboxylic acids of the skeleton of DTPA. CA 2,177,977 discloses a number of complex derivatives of DTPA which carry huge substituents containing one or more aromatic moieties, which are especially suitable for diagnostic radiology of the liver.

No mention is found in this prior-art on the possibility that said compounds form strong non-covalent bonds with the serum/plasma proteins, turning out to be useful also as blood pool contrast agents. In fact the fact that said compounds are substantially hepatospecific means that they are preferentially, if not selectively taken up by the liver hepatocytes and are then excreted via the biliary route, thus being cleared away from the vessels in a very short time.

SUMMARY OF THE INVENTION

The compounds of the present invention are diethylenetriaminepentaacetic acid derivatives characterised by having a hindering group in a to at least one of the 5 DTPA carboxylic groups wherein said substituent has the dimension of a $C_1$–$C_{20}$ alkyl, linear or branched, saturated or unsaturated chain, which is substituted or interrupted by at least two cyclic, optionally aromatic, carbocyclic or eterocyclic, saturated or unsaturated, isolated or fused units.

Particularly preferred compounds are those having one hindering group in the α position of the central carboxylic acid of the DTPA skeleton, in particular the ones in which said hindering group is a tyrosine residue.

Said hindering group is probably responsible for the interaction of the paramagnetic chelates with biological components of the fluids in which the agent diffuses, wherein said interaction produces the surprisingly high relaxivity values that we have measured in Human Reconstructed Serum.

Relaxivity values of the contrast agent of the present invention have been tested either in saline or in human serum obtained by Seronorm™ Human, freeze-dried human serum produced by Nycomed Pharma AS, Oslo, Norway. Serum obtained from said Seronorm™ is substantially equivalent to the fresh one, so its use in the relaxivity determination grants a good picture of the "in vivo" behaviour and, further, an excellent reproducibility of this test.

The compounds object of the present invention are characterised by very high $r_1$ and $r_2$ relaxivity values. When measured in Seronorm™ Human at 20 MHz, at a temperature of 39° C., and at a concentration comprised from 0 to 1 mM, compounds of the present invention usually have $r_1$ relaxivity equal to or, preferably, higher than $15^{s-1}mM^{-1}$, thus confirming the formation of unexpectedly strong non-covalent bonds with serum proteins. This feature has been further confirmed by measuring the protein binding of the chelate complexes of the invention to Human Serum Albumin (HSA), whereas an average percent binding value superior to 80% was found. Last, significative amounts of the preferred compounds of the invention have also been found in the urines, showing that, thanks to their binding to HSA, the same are very promising as blood pool diagnostic agents.

DETAILED DISCLOSURE OF THE INVENTION

The present invention relates to novel chelating agents, more particularly linear aminopolycarboxylic acid derivatives chelants, and metal chelates thereof and the use of such chelating agents and chelates in the preparation of diagnostic imaging contrast agents and in particular of contrast agents exhibiting improved serum relaxivity.

Said compounds are polyaminopolycarboxylic acid derivatives of formula (I)

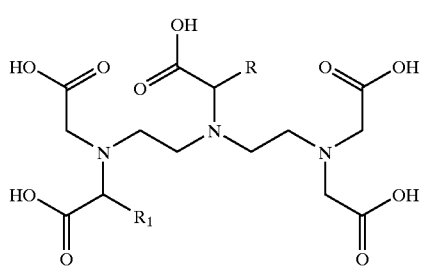

(I)

in which:
  R is H, or a linear or branched, saturated or unsaturated $C_1$–$C_{20}$ alkyl, optionally interrupted by one or more —CH(OH)—, —CONH—, —NHCO—, —CO—, —CH(NH$_2$)—, —SO—, —SO$_2$—, SO$_2$NH— groups and/or one or more N, O, S atoms, optionally substituted with one or more —COOH groups and/or amide or ester derivatives thereof, and in which said alkyl chain is interrupted or substituted by at least 2, which are independently the same or different, isolated or fused, cyclic L residues, with the proviso that, when some L residues are fused together, the resulting polycyclic unit comprises no more than 3 cyclic group, and in which
  L is a carbocyclic or heterocyclic, saturated or unsaturated or aromatic cyclic unit, comprising from 5 to 6 atoms, optionally substituted by one or more X groups, which are independently the same or different, in which
  X is OH, halogen, NH$_2$, NHZ, N(Z)$_2$, —OZ—, —SZ, —COZ, where the Z groups can independently be a $C_1$–$C_5$ linear or branched alkyl, optionally substituted with one or more —OH, —COOH or alkoxy groups, or said X group is a —COOH group or a derivative thereof, such as an ester or an amido group, or an —SOZH group or an amido derivative of the same;
  $R_1$ is the same as R with the provisos that:
  R and $R_1$ cannot be at the same time H;
  when R is different from H, $R_1$ is H;
  when $R_1$ is different from H, R is H.

The compounds comprised within formula (I) can be either racemic or optically active.

The invention further comprises complexes of the ligand of formula (I) with metal ions of atomic number from 20 to 31, 39, from 42 to 44, 49 and from 57 to 83; particularly preferred metals being: $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$, $Mn^{(2+)}$; as well as, where the metal chelate carries an overall charge, a salts thereof with a physiologically acceptable counterion, preferably selected from organic bases such as a primary, secondary or tertiary amines, a basic amino acid, or an inorganic base derived from an alkali metal or alkaline-earth metal cation such as: $Na^+$, $K^+$, $Mg^{2+}$, $Ca^{2+}$ or a mixture thereof.

The present invention further relates to the use of the compounds of formula (I) and of the salts of the complexes thereof as well as the pharmaceutical formulations containing them for a diagnostic or therapeutic scope.

Particularly preferred is their use as contrast agents in a method of performing the diagnostic imaging of the blood pool compartment.

Preferred are the compounds of formula (I) in which R or $R_1$ are selected from the following groups:

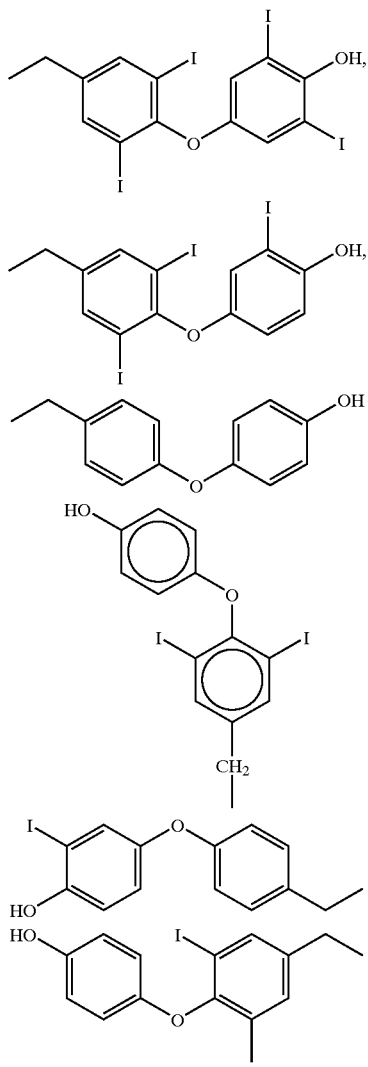

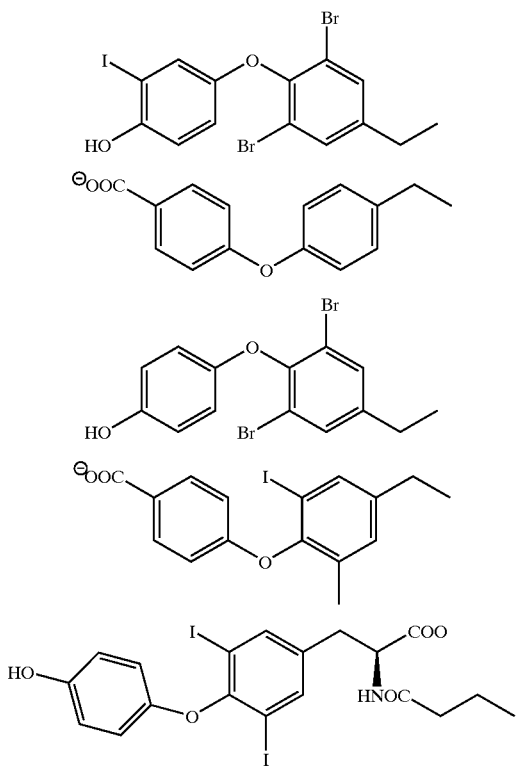

Among the compounds of formula (I) particularly preferred are the ones of formula (II),

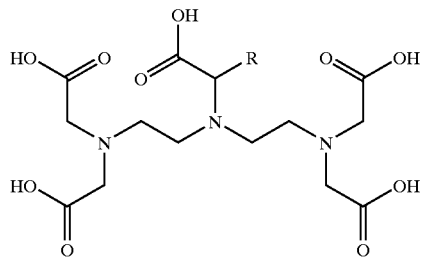

in which R1 is H and R is as defined above in formula (I), but is different from H.

Among compounds of formula (II), preferred are the compounds of formula (III):

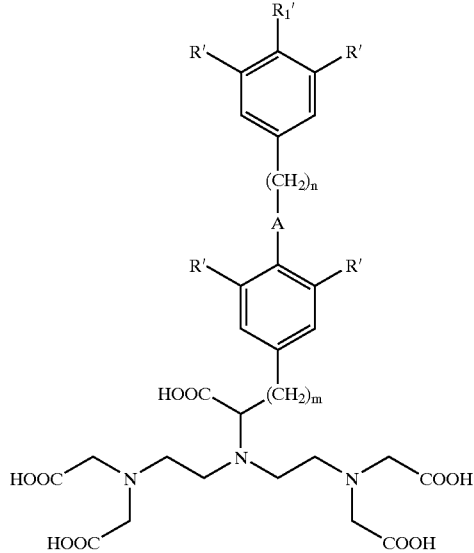

wherein:
R'=independently H, halogen;
R'$_1$=H, OH, N(R")$_2$, COOR", —CON(R")$_2$, —SO3H, —SO$_2$NHR", C$_1$–C$_6$ alkyl, C$_1$–C$_6$ alkoxy;
A=direct bond (i.e. non intervening atom), —O—, C=O
m=integer 1–6;
n=integer 0–2;
R"=independently H or C$_1$–C$_5$ linear or branched alkyl, optionally substituted with 1 to 5 —OH groups;
with the proviso that, when R'$_1$=H, at least one of the substituents R' is different from hydrogen.

Among compounds of formula (III), particularly preferred are the compounds of formula (IV)

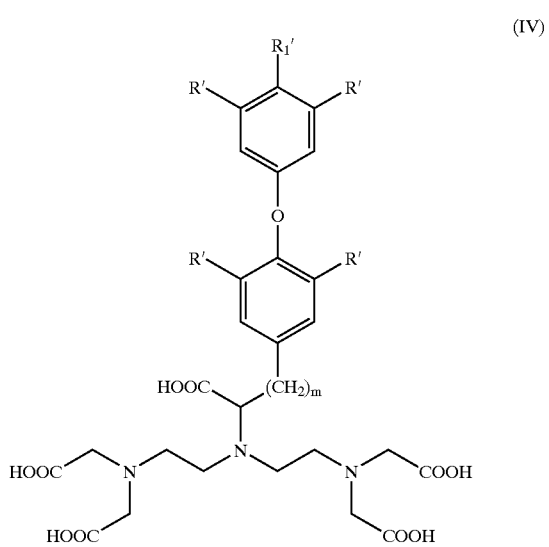

where:
R'=independently H, halogen;
R'$_1$=H, OH, N(R")$_2$, COOR", —CON(R")$_2$, —SO$_3$H, —SO$_2$NHR", C$_1$–C$_6$ alkyl, C$_1$–C$_6$ alkoxy;
m=integer 1–6;
R"=independently H or C$_1$–C$_5$ linear or branched alkyl, optionally substituted with 1 to 5 —OH groups;
with the proviso that at least one of the substituents R' is different from hydrogen,
as well as compounds of formula (V)

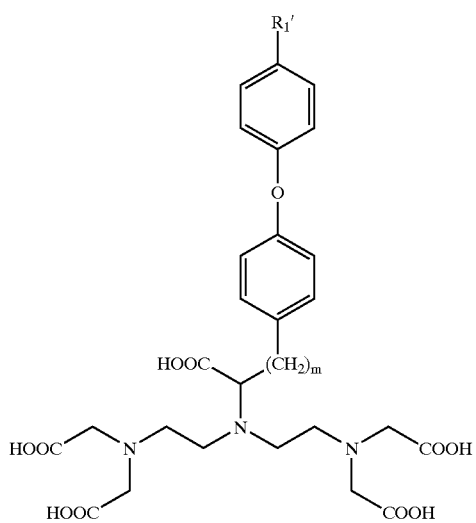
(V)

where:
R'$_1$=OH, N(R")$_2$, COOR", —CON(R")$_2$, —SO$_3$H, —SO$_2$NHR", C$_1$–C$_6$ alkyl, C$_1$–C$_6$ alkoxy;
m=integer 1–6;
R"=independently H or C$_1$–C$_5$ linear or branched alkyl, optionally substituted with 1 to 5 —OH groups.

Among compounds of formula (II), preferred are also those of formula (VI)

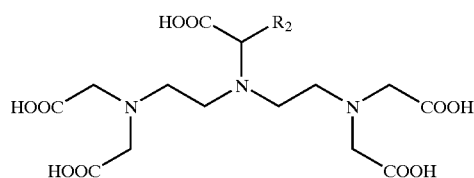
(VI)

where:
R$_2$=C$_1$–C$_8$ alkyl, optionally interrupted by one or more —CONH—, —NHCO—, —CO— groups and/or N, S atoms, optionally substituted with —OH, —COOH, —NH$_2$, —N(R")$_2$ groups, said alkyl being interrupted or substituted with a polycyclic unit comprising from 2 to 3 saturated or unsaturated or aromatic fused rings, said polycyclic unit being interrupted by one or more N, O, S and optionally substituted with —OH, —COOH, —NH$_2$, —N(R")$_2$, C$_1$–C$_6$ alkyl, C$_1$–C$_6$ alkoxy, C$_6$–C$_{20}$ arylalkoxy groups;
R"=independently H or C$_1$–C$_5$ linear or branched alkyl, optionally substituted with 1 to 5 —OH groups;
and particularly preferred are the compounds of general formula (VII)

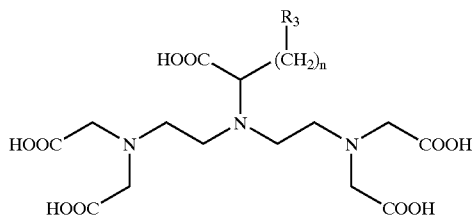
(VII)

in which:
R$_3$=a polycyclic unit comprising from 2 to 3 saturated or unsaturated or aromatic fused rings, said polycyclic unit being interrupted by one or more N, O, S and optionally substituted with —OH, —COOH, —NH$_2$, —N(R")$_2$, C$_1$–C$_6$ alkyl, C$_1$–C$_6$ alkoxy, C$_6$–C$_{20}$ arylalkoxy groups;
R"=independently H or C$_1$–C$_5$ linear or branched alkyl, optionally substituted with 1 to 5 —OH groups;
n=integer 1–6.

Two further groups of preferred compounds, comprised within formula (II), are the compounds of formula (VIII)

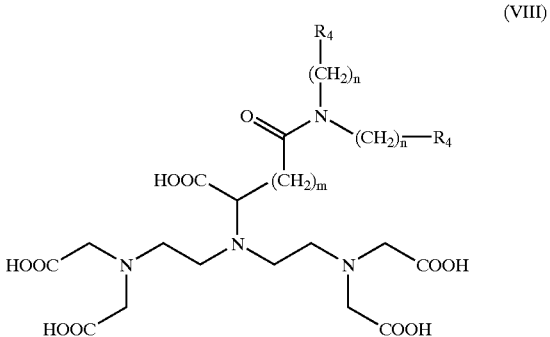
(VIII)

in which:
m=integer from 1 to 4;
n=independently integer from 0 to 2;
R4=independently saturated, unsaturated or aromatic ring, optionally interrupted by one or more N, O, S atoms and optionally substituted with one or more —OH, —COOH, —NH$_2$, —N(R")$_2$, —CON(R")$_2$, —SO$_3$H;
R"=independently H or C$_1$–C$_5$ linear or branched alkyl, optionally substituted with 1 to 5 —OH groups;
and the compounds of formula (IX)

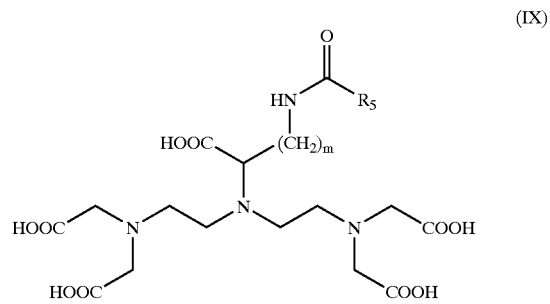
(IX)

in which:
R$_5$=C$_1$–C$_3$ alkyl, interrupted or substituted with 2 to 3 saturated, unsaturated or aromatic, isolated or fused rings, that are optionally interrupted by one or more N, O, S and optionally substituted with one or more —OH, —COOH, —NH$_2$, —N(R")$_2$, —CON(R")$_2$, —SO$_3$H;

R"=independently H or C$_1$–C$_5$ linear or branched alkyl, optionally substituted with 1 to 5 —OH groups;

m=1–6.

Among compounds of general formula (IX), particularly preferred are the compounds of formula (X)

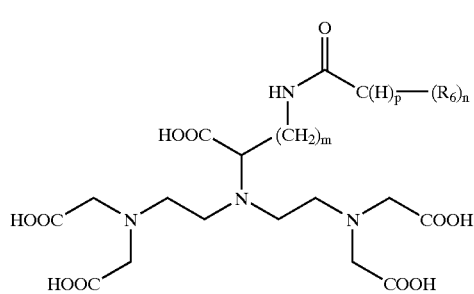

(X)

in which:

R$_6$=saturated, unsaturated or aromatic 5- or 6-membered ring, optionally interrupted by one or more N, O, S;

m=1–6;

n=2 or 3;

p=0 or 1;

with the proviso that p+n=3.

Among the compounds of formulae (III) and (IV), most preferred are the compounds from 1 to 3 of formula:

compound 1

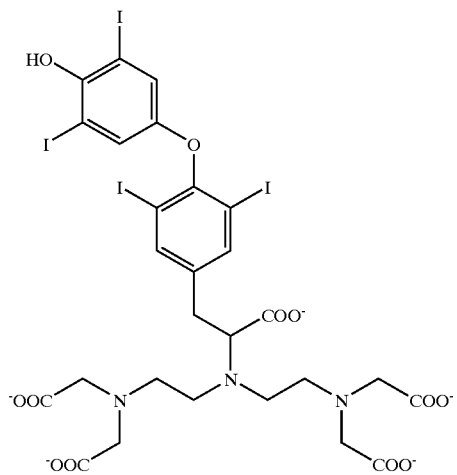

compound 2

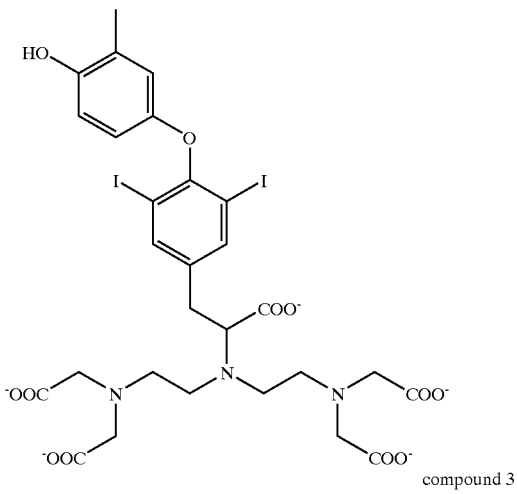

compound 3

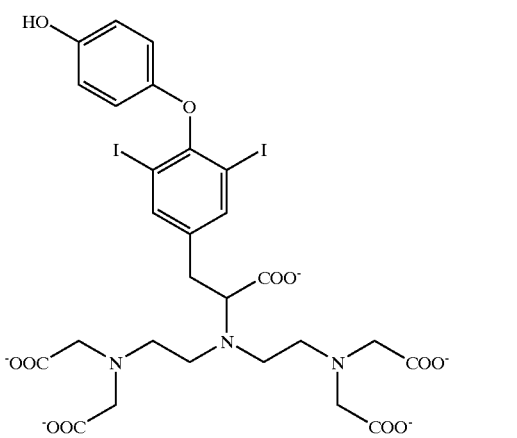

Among the compounds of formula (V), most preferred is compound 4 of formula:

compound 4

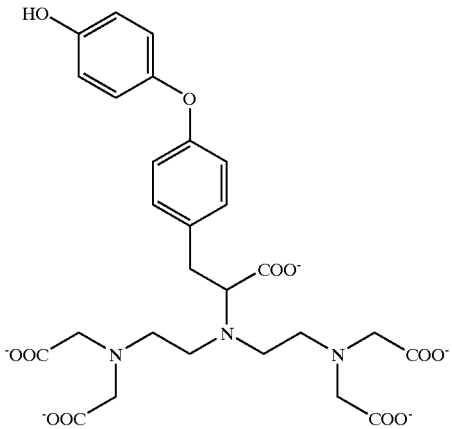

Among the compounds of formula (VI), most preferred is compound 5 of formula:

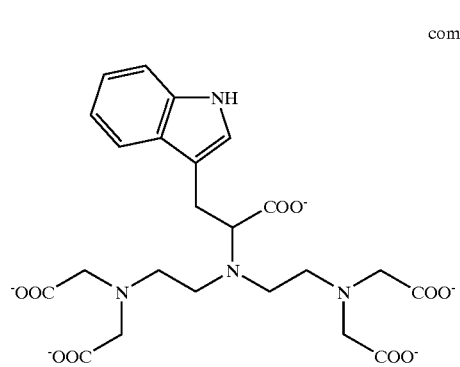
compound 5

Among the compounds of formula (VII), most preferred is compound 6 of formula:

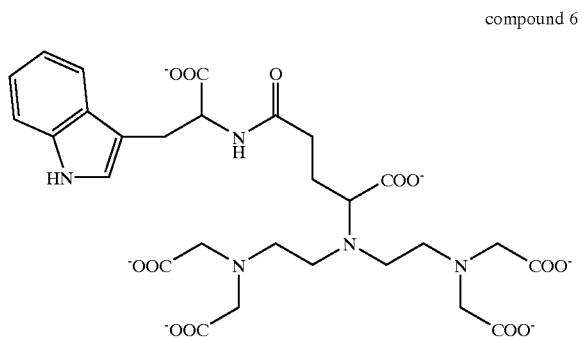
compound 6

Among the compounds of formula (VIII), most preferred are compounds 7 and 8, respectively of formula:

compound 7

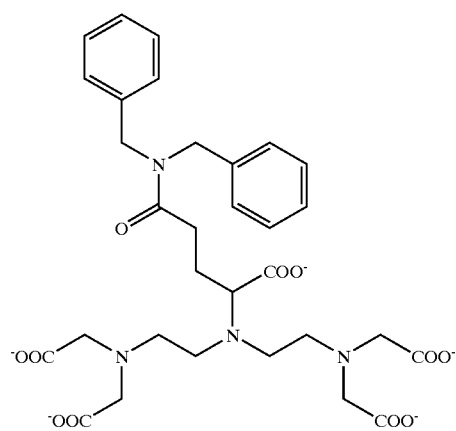

compound 8

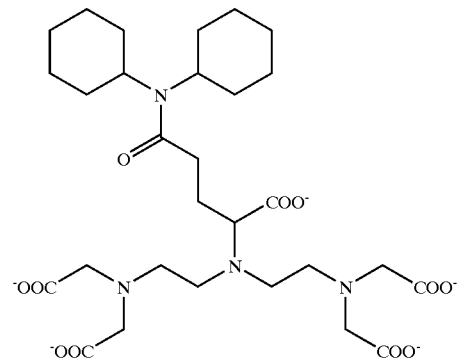

and among the compounds of formulae (IX) and (X), most preferred are compounds from 9 to 11 of formulae compound 9

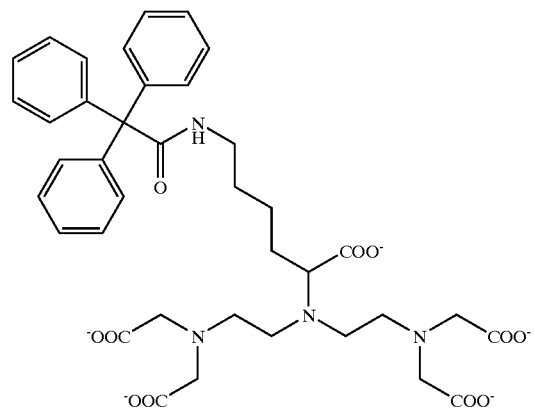

compound 10

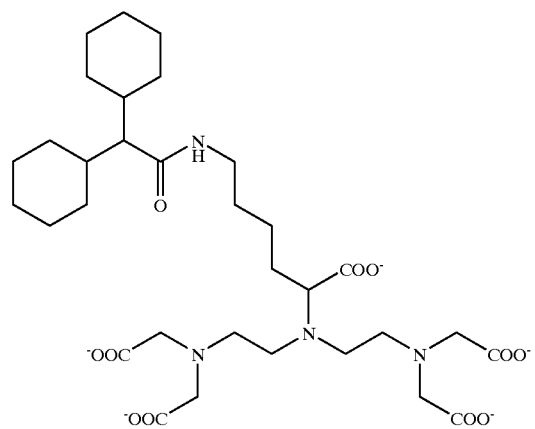

compound 11

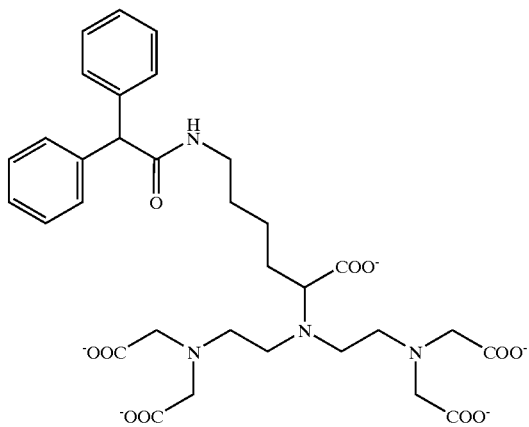

respectively.

The preparation of the compounds of the present application comprises the regiospecific introduction of the hindering substituent in a to a carboxylic group of the acetic acid bound to the central nitrogen atom of DTPA.

One of the preferred synthetical ways used refers to that introduced by Rapoport (J. Org. Chem. 1993, 58, 1151–1158), starting from natural or synthetical à-amino acid derivatives. An alternative way comprises the use of synthons such as glutamic acid or lysine, which allows the introduction of hindering groups quite distant from the carbon atom in à to a carboxylic group of the central acetic acid residue, exploiting the terminal acid or amino functions, respectively, of a.m. amino acids.

Starting from suitable precursor synthons it is also possible make use of the synthesis disclosed in U.S. Pat. No. 5,514,510.

As far as the introduction of the hindering substituent at the à- position to the carboxylic group of one of the acetic groups bound to the side nitrogen atoms of DTPA is concerned, the synthesis scheme below can be followed:

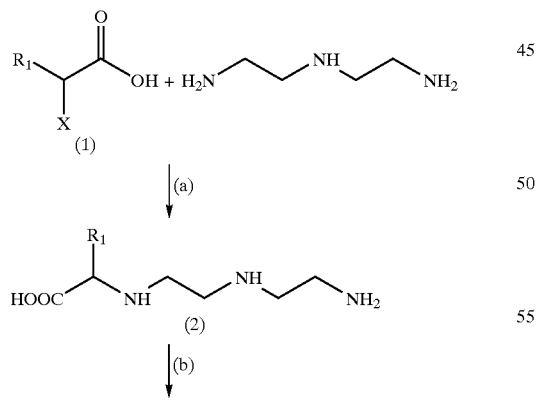

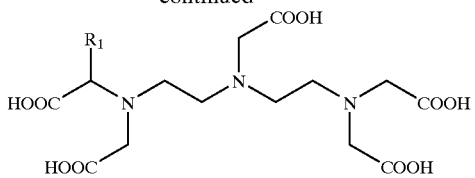

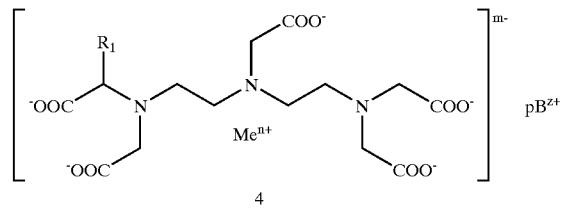

wherein $R_1$ is as defined above for compounds of general formula (I).

The synthesis comprises the following steps:

(a) precursor (1), wherein X=Cl, Br or other leaving groups, is reacted with a diethylenetriamine excess in water, at a temperature of about 50° C., to obtain almost selectively compound (2), which is reacted in step (b) with sodium bromoacetate in water at pH 10, to give the pentaacid (3), which is reacted, in the subsequent step (c) with a suitable oxide or salt of a metal having atomic number comprised from 20 to 31, 39, from 42 to 44, 49 and from 57 to 83 (such as $Gd_2O_3$, $GdCl_3$) e with the appropriate amount of a physiologically acceptable organic base (such as meglumine) or of an inorganic base the cations of which are sodium, potassium, magnesium, calcium, or mixtures thereof, to give the final compound (4), wherein:

$Me^{n+}$=ion of the metal element having atomic number comprised from 20 to 31, 39, from 42 to 44, 49 and from 57 to 83 (such as $Gd^{3+}$);

n=number of the positive charges of said ion;

m=number of the overall negative charges of the metal chelate;

$B^{z+}$=$Na^+$, $K^+$, $Mg^{++}$, $Ca^{++}$ or mixtures thereof, or it is the salt of a physiologically acceptable organic base;

z=number of the positive charges of B;

p=an integer so that: p×z=m.

TABLE 1

| Compound | Structure | Relaxivity (mM⁻¹s⁻¹) | | | |
| --- | --- | --- | --- | --- | --- |
| | | Saline (*) | | Serum (**) | |
| | | $r_1$ | $r_2$ | $r_1$ | $r_2$ |
| Gd-DTPA/Dimeg | [structure: Gd³⁺·2MegH⁺] | 3.77 | 4.73 | 4.96 | 5.43 |
| Gd-BOPTA($)/Dimeg | [structure: Gd³⁺·2MegH⁺] | 4.39 | 5.56 | 10.8 | 12.2 |
| Gd-EOB-DTPA(+)/Dimeg | [structure: 2 MegH⁺, Gd³⁺] | 5.43 | 6.15 | 11.00 | 12.60 |
| Compound 1 Gd complex, dimeg. salt | [structure] | 17.0 | 19.0 | 34.3 | 39.6 |

Table I above discloses the high relaxivity shown in serum by the compounds of the present application; $r_1$ and $r_2$ relaxivity values of some of the preferred compounds are reported, in comparison with the corresponding $r_1$ and $r_2$ values measured for some of the mayor prior-art compounds: Gd-DTPA Dimeglumine salt (MAGNEVIST®); Gd-BOPTA Dimeglumine salt and Gd-EOB-DTPA Dimeglumine salt.

The data of Table 1 clearly show that the compounds of the present invention have surprisingly high relaxivity values $r_1$ and $r_2$, measured in Seronorm™ Human.

The same experiments were performed on the chelate complex compounds described in Examples 11 to 17 (Compounds 12 to 18). Values of $r_1$ and $r_2$, measured in Seronorm™ Human are superior to 31 and 35, respectively. The percentual binding to HSA is on average superior to 80% up to 97%. The urinary elimination in rats is even superior to 38%, for some of the preferred compounds.

This is particularly interesting from the application point of view, both as far as the improvement in the obtainable images, the development of formulations specific to particular districts, i.e. the blood pool district, and the determination of optimum low dosages of the contrast medium are concerned.

EXAMPLE 1

N-(2-Bromoethyl)-N-[2-(1,1-dimethylethoxy)-2-oxoethyl]glycine 1,1-Dimethylethyl Ester

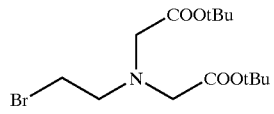

Ethanolamine (15.15 g; 0.25 mol) was dropped in 10 minutes into a suspension of t-butyl bromoacetate (112.3 g; 0.58 mol) and KHCO3 (62.57 g; 0.62 mol) in DMF (400 mL), maintained at 0° C. under inert atmosphere. After 22 h at 20° C. the suspension was diluted with a saturated solution of NaHCO3 (400 mL) and Et2O (400 mL). After separation, the aqueous phase was extracted with Et2O (800 mL); the organic phases were collected, dried (Na2SO4) and concentrated. The obtained oil (100 g) was dissolved in CH2Cl2 (700 mL), then triphenylphosphine was added (79, 76 g; 0,30 mol). To the solution, cooled to 0° C., solid NBS was slowly added (53,4 g; 0,30 mol). After 2.5 h the solution was concentrated to dryness and diluted with Et2O (500 mL); the salts were filtered off, the solution was diluted with Et2O (500 mL), then left at 4° C. for 16 h. The salts were filtered off and the solution was concentrated; the oily residue (100 g) was purified by flash chromatography (silica gel; 95:5 n-hexane/EtOAc). The fractions having comparable purity were collected and evaporated to dryness, obtaining the desired compound (57 g; 0,16 mol). Yield 65%.

Gaschromatographic titre: 99% (area %)–Chromatographic method: Stationary phase: DB 5 (OV-73); Film thickness: 0,25 μm; Column: 30 m×0,25 mm; He flow rates at 130° C.:

| column flow rate | 0.9 mL.min$^{-1}$; |
|---|---|
| split flow rate | 100 mL.min$^{-1}$; |
| column flow rate + make-up | 30 mL.min$^{-1}$; |
| septum purge flow rate | 3 mL.min$^{-1}$; |

Detector feeding (FID):

| H$_2$ pressure | 1.2 bar; |
|---|---|
| Air pressure | 2.8 bar; |
| Temperature timetable: | |
| 1$^{st}$ isotherm | 50° C. for 0 min; |
| gradient | 10° C. min$^{-1}$; |
| 2$^{nd}$ isotherm | 150° C. for 10 min; |

Injector temperature: 150° C.; Detector temperature: 200° C.; Injection: 1 μL; Sample concentration: 30 mg.mL$^{-1}$ TLC: Rf 0,4 Stationary phase: silica gel Mobile phase: 9:1 n-hexane: EtOAc (v/v) Detection: 0.5% KMnO4 (w/w) in 1 N NaOH $^{13}$C-NMR, $^1$H-NMR, MS and IR spectra were consistent with the structure. K.F.: 0,1% (w/w); Elemental analysis (%):

| | C | H | N | Br |
|---|---|---|---|---|
| Calcd. | 47.73 | 7.44 | 3.98 | 22.68 |
| Found | 47.86 | 7.50 | 4.03 | 22.49 |

EXAMPLE 2

N$^2$,N$^2$-Bis[2-[bis[2-(1,1-Dimethylethoxy)-2-oxoethyl]amino]ethyl]L-lysine 1,1-Dimethylethyl Ester

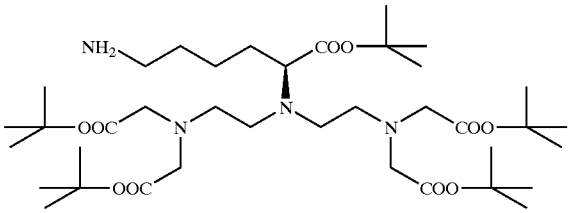

A) N$^6$-[(Phenylmethoxy)carbonyl]-L-lysine-1,1-dimethylethylester C.A.S. [21957-42-6]

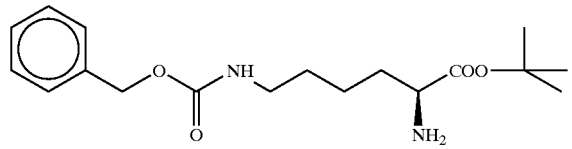

The compound was prepared according to: Bentley, P. H.; Stachulski, A. V. J. Chem. Soc. Perkin Trans. I 1983, 1187–1192.

B) N$^6$-[(Phenylmethoxy)carbonyl]-N$^2$,N$^2$-bis[2-[bis[2-(1,1-dimethylethoxy)-2-oxoethyl]amino]ethyl]-L-lysine 1,1-dimethylethyl Ester

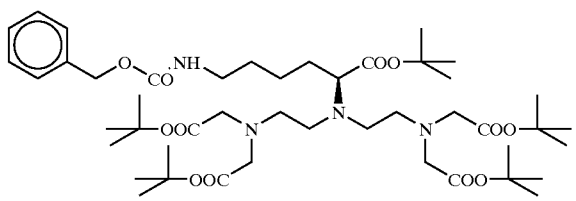

N<sup>6</sup>-[(Phenylmethoxy)carbonyl]-L-lysine 1,1-dimethylethyl ester (80.6 g; 0.24 mol) and N-(2-bromoethyl)-N-[2-(1,1-dimethylethoxy)-2-oxoethyl]glycine 1,1-dimethylethyl ester (209 g; 0.59 mol) (prepared according to Example 1) were dissolved in MeCN (900 mL). After addition of 2 M pH 8 phosphate buffer (1000 mL) the mixture was vigorously stirred for 2 h. The two phases were separated and the aqueous phase replaced with fresh 2 M pH 8 phosphate buffer (80 mL). After stirring for 48 h the mixture was separated and the organic phase concentrated to dryness, to give a residue which was dissolved in $CH_2Cl_2$ (1000 mL). The solution was washed with $H_2O$ (2×50 mL), then dried and concentrated to yield an oil which was purified by silica gel chromatography:

Silica gel column; Stationary phase: Silica gel 230–400 mesh Merck KGaA art. 9385; Mobile phase 4:1 n-hexane/EtOAc.

The desired product (190 g; 0.216 mol) was obtained. Yield 90%.

The product was utilised for the following step without further purification.

Acidic titer (0.1 N $HClO_4$ in $CH_3COOH$): 96.8%; TLC: Rf 0.22; Stationary phase: Silica gel plates 60 $F_{254}$ Merck KGaA art 5715; Mobile phase: 2/1 n-hexane/EtOAc; Detection: 1% $KMnO_4$ in 1 N NaOH; HPLC: 95.1% (area %)–Chromatographic method: Stationary phase: Lichrosorb RP—Select B 5 μm; 250×4 mm column packed by Merck KGaA; Temperature: 45° C.; Mobile phase: gradient elution; A=0.01 M $KH_2PO_4$ and 0.017 M $H_3PO_4$ in water; B=$CH_3CN$;

| Gradient timetable: | min | % A | % B |
| --- | --- | --- | --- |
|  | 0 | 90 | 10 |
|  | 35 | 40 | 60 |
|  | 40 | 40 | 60 |
|  | 43 | 30 | 70 |
|  | 50 | 30 | 70 |

Flow rate: 1 mL min$^{-1}$; Detection (UV): 210 nm; Injection: 10 μL; Sample concentration: 1 mg mL$^{-1}$; Instrumentation: Merck KGaA—Hitachi high pressure gradient pump system (two Lachrom L 7100 pumps), Merck KGaA—Hitachi Lachrom L 7200 autosampler, Merck KGaA—Hitachi Lachrom L 7300 column thermostat, Merck KGaA—Hitachi Lachrom L 7400 UV detector. K.F.: <0.10%; $^{13}$C-NMR, $^1$H-NMR, MS and IR spectra were consistent with the structure. $[\alpha]^{20}$(c 4.98; $CHCl_3$);

| λ (nm) | 589 | 578 | 546 | 436 | 405 | 365 |
| --- | --- | --- | --- | --- | --- | --- |
| $[\alpha]^{20}_\lambda$ | −26.40° | −28.03° | −32.13° | −57.81° | −71.44° | −98.57° |

Elemental analysis (%):

|  | C | H | N |
| --- | --- | --- | --- |
| Calcd. | 62.85 | 8.94 | 6.37 |
| Found | 63.04 | 9.20 | 6.27 |

C) N$^2$,N$^2$-bis[2-[bis[2-(1,1-Dimethylethoxy)-2-oxoethyl]amino]ethyl]-L-lysine 1,1-dimethylethyl Ester To a solution of the product from the previous preparation (180 g; 0.2 mol) in MeOH (1 L), 5% Pd on carbon (commercial product) (9 g) was added. The suspension was stirred for 4 h under a hydrogen atmosphere at 20° C. (consumed H2 3900 mL; 0.174 mol). The mixture was filtered over Millipore® HA 0.45 æm, washed with MeOH and the solution was evaporated. The residue was dissolved in 0.5 N HCl and the solution was maintained under vacuum for 10 min, then 1 N NaOH was added and the product was extracted with $Et_2O$. The solution was evaporated and the residue was purified by silica gel chromatography:

Silica gel column; Stationary phase: Silica gel 230–400 mesh Merck KGaA art 9385 (600 g); Mobile phase: MeOH; The desired compound (90 g; 0.121 mol) was obtained. Yield 60%; Acidic titer (0.1 N HCl): first inflection point 93.7%; Second inflection point 95.3%; Equivalent points pH 7.3 and 7.8; TLC: Rf 0.08; Stationary phase: Silica gel plates 60 $F_{254}$ Merck KGaA art 5715; Mobile phase: MeOH; Detection: 1% $KMnO_4$ in 1 N NaOH; $^{13}$C-NMR, $^1$H-NMR, MS and IR spectra were consistent with the structure. $[\alpha]^{20}$(c 5.07; $CHCl_3$);

| λ (nm) | 589 | 578 | 546 | 436 | 405 | 365 |
| --- | --- | --- | --- | --- | --- | --- |
| $[\alpha]^{20}_\lambda$ | −27.19° | −28.77° | −33.24° | −59.98° | −74.88° | −104.67° |

Elemental analysis (%):

|  | C | H | N |
| --- | --- | --- | --- |
| Calcd. | 61.26 | 9.74 | 7.52 |
| Found | 61.43 | 10.25 | 7.48 |

EXAMPLE 3

(S)-5-oxo-3-[(Phenylmethoxy)carbonyl]-4-oxazolidinepropanoyl Chloride

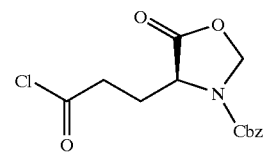

A) N-[(Phenylmethoxy)carbonyl]-L-glutamic Acid

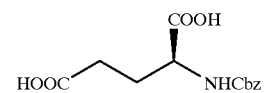

A suspension of L-glutamic acid (23.5 g; 160 mmol) in $H_2O$ (100 mL) was stirred, maintaining the pH at 8.5 with 10 M NaOH until complete dissolution. Benzyl chloroformate (35 g; 205 mmol) was added over 15 min to the clear solution. The mixture was stirred, maintaining the pH at 9 by adding 10 M NaOH until the reaction was complete. The cloudy mixture was washed with Et$_2$O (3×150 mL) and then the pH of the resulting solution was adjusted to 2.1 with 1 M HCl. The cloudy aqueous mixture was extracted with Et$_2$O (2×200 mL), the organic layers were collected and evaporated to yield the desired product (39.13 g; 139 mmol). Yield 87%.

HPLC : 97% (area %)–Chromatographic method: Stationary phase: Lichrosorb RP-Select B 5 μm; 250×4 mm column packed by Merck KGaA; Temperature: 45° C.; Mobile phase: gradient elution; A=0.017 M H$_3$PO$_4$ in water; B=CH$_3$CN;

| Gradient timetable: | min | % A | % B |
|---|---|---|---|
| | 0 | 95 | 5 |
| | 5 | 95 | 5 |
| | 30 | 20 | 80 |
| | 45 | 20 | 80 |

Flow rate: 1 mL min$^{-1}$; Detection (UV): 210 nm; Injection: 10 μL; Sample concentration: 1 mg mL$^{-1}$; Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 4000 UV detector. TLC: Rf 0.3; Stationary phase: Silica gel plates 60 F$_{254}$ Merck KGaA art 5715; Mobile phase: 6:3:1 CHCl$_3$:MeOH:25% aq. NH$_4$OH; Detection: 1% KMnO$_4$ in 1 M NaOH.

B) (S)-5-oxo-3-[(Phenylmethoxy)carbonyl]-4-oxazolidinepropanoyl Chloride

A suspension of the product from the previous preparation (30 g; 107 mmol), paraformaldehyde (6 g) and PTSA (0.3 g) in toluene (400 mL) was refluxed in a Dean Stark trap. When the water evolution was over the hot cloudy mixture was filtered and the resulting clear solution was evaporated under reduced pressure (2 kPa). The oily residue was dissolved in SOCl$_2$ (150 mL). The mixture was stirred at r.t. for 3 h, then carefully evaporated under reduced pressure (2 kPa) to yield an oil that became solid on standing overnight at 4° C. The crude was slurried with hexane (200 mL) and then with Et$_2$O (150 mL) to yield the title compound (21.7 g; 69 mmol). Overall yield 65%.

HPLC: 95.7% (area %)–Chromatographic method: the same of previous step A);

Argentometric titer (0.1 M AgNO$_3$): 98.2%;

EXAMPLE 4

[[N,N-bis[2-[bis(Carboxymethyl)amino]ethyl]-O-(4-hydroxyphenyl)-3,5-diiodo-L-tyrosinato(5-)] gadolinate(2-)]dihydrogen Compound with 1-Deoxy-1-(methylamino)-D-glucitol (1:2)

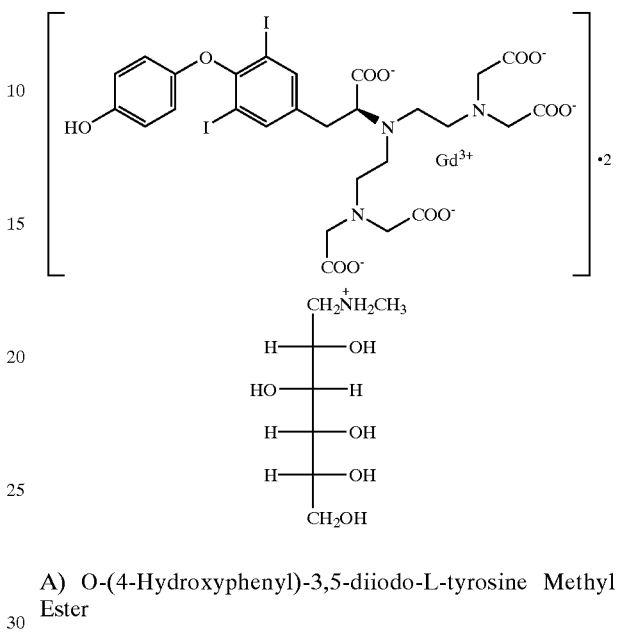

A) O-(4-Hydroxyphenyl)-3,5-diiodo-L-tyrosine Methyl Ester

A 6 M solution of HCl in MeOH (8 mL; 4.8 mmol) was added to a suspension of O-(4-hydroxyphenyl)3,5-diiodo-L-tyrosine (2.12 g; 5 mmol) (prepared according to: Chalmers J. R., Dickson G. T., Elks J. and Hems D. A., "The Synthesis of Thyroxine and Related Substances", Part V., J. Chem. Soc. (1949), 3424–3433) in MeOH (12 was stirred for 4 days at 20° C. Then a NaHCO$_3$ saturated aqueous solution was added to the mixture until pH 7 was reached, obtaining a precipitate which was filtered by concentration of the solution a second crop of precipitate was obtained. The two samples were combined and dried (50° C.; 1.3 kPa) 3.7 mmol). Yield 87%.

mp: 173° C.; Acidic titer (0.1 M HClO$_4$): 96.1%; HPLC: 98.4% (area %)–Chromatographic method: Stationary phase: Lichrosorb RP-Select B 5 mm; 250×4 mm column packed by Merck KGaA; Temperature: 45° C.; Mobile phase: gradient elution; A=0.017 M H$_3$PO$_4$ in water; B=CH$_3$CN;

| Gradient timetable: | min | % A | % B |
|---|---|---|---|
| | 0 | 95 | 5 |
| | 5 | 95 | 5 |
| | 30 | 20 | 80 |
| | 45 | 20 | 80 |

Flow rate: 1 mL min$^{-1}$; Detection (UV): 210 nm; Injection: 10 μL; Sample concentration: 1 mg mL$^{-1}$; Instrumentation:

Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector.

TLC: Rf 0.64; Stationary phase: Silica gel plates 60 $F_{254}$ Merck KGaA art 5715; Mobile phase 9:1 $CH_2Cl_2$:MeOH; Detection 1% $KMnO_4$ in 1 M NaOH; $^{13}C$-NMR, $^1H$-NMR and MS spectra were consistent with the structure. KF: 044%; Elemental analysis (%);

|  | C | H | I | N | Cl |  |
|---|---|---|---|---|---|---|
| Calcd. | 36.65 | 2.80 | 47.08 | 2.60 | — |  |
| Found | 35.32 | 2.72 | 45.60 | 2.57 | <0.1 | anhydrous |

B) N,N-bis[2-[bis[2-(1,1-Dimethylethoxy)-2-oxoethyl] amino]ethyl]-O-(4-hydroxyphenyl)-3,5-diiodo-L-tyrosine Methyl Ester

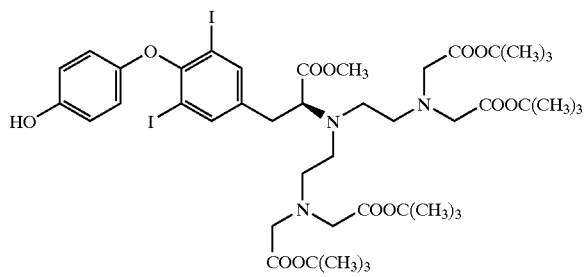

The ester from the previous preparation (34 g; 95 mmol) and N-(2-bromoethyl)-N-[2-(1,1-dimethylethoxy)-2-oxoethyl]glycine 1,1-dimethylethyl ester, prepared according to Example 1, (67 g; 190 mmol) were dissolved in $CH_3CN$ (1 L) and 2M H 7 phosphate buffer (1 L) was then added. The mixture was vigorously stirred for 2 days then, after separation, further N-(2-bromoethyl)-N-[2-(1,1-dimethylethoxy)-2-oxoethyl]glycine 1,1-dimethylethyl ester (10 g; 28 mmol) and fresh 2M pH 7 phosphate buffer (1 L) were added to the organic phase and the mixture was stirred for 16 h. After a further addition of N-(2-bromoethyl)-N-[2-(1,1-dimethylethoxy)-2-oxoethyl]glycine1,1-dimethylethyl ester (13 g; 37 mmol) the mixture was stirred for 8 h. After separation the organic phase was evaporated to dryness (35° C.; 1.3 kPa). The residue was suspended in $CH_2Cl_2$ (750 mL) and washed with brine (260 mL) and with $H_2O$ (30 mL). The clear organic phase was dried ($Na_2SO_4$) and evaporated to yield an oil (125 g) which was purified by flash chromatography (Stationary phase: silica gel 230–400 mesh Merck KGaA art 9385 (1 kg; 100×250 mm). Mobile phase: 7:3 n-hexane: EtOAc (10 L)). The desired compound was obtained (77 g; 71 mmol). Yield 75%.

Acidic titer (0.1 M HClO4): 96.4%; TLC: Rf 0.28; Stationary phase: Silica gel plates 60 $F_{254}$ Merck KGaA art 5715; Mobile phase: 7:3 n-hexane:EtOAc; Detection: 1% $KMnO_4$ in 1 M NaOH; HPLC: 98% (area %) Chromatographic method: the same of previous step A) $^{13}C$-NMR, $^1H$-NMR, MS and IR spectra were consistent with the structure. $[\alpha]^{20}$(c 0.98; $CHCl_3$):

| λ (nm) | 589 | 578 | 546 | 436 | 405 | 365 |
|---|---|---|---|---|---|---|
| $[\alpha]^{20}_\lambda$ | −35.69° | −38.64° | −44.13° | −79.21° | −97.62° | −134.47° |

KF: 0.29%; Elemental analysis (%):

|  | C | H | I | N |  |
|---|---|---|---|---|---|
| Calcd. | 48.85 | 6.06 | 23.46 | 3.88 |  |
| Found | 49.13 | 6.18 | 22.99 | 3.85 | anhydrous |

C) N,N-bis[2-[bis(Carboxymethyl)amino]ethyl]-O-(4-hydroxyphenyl)-3,5-diiodo-L-tyrosine

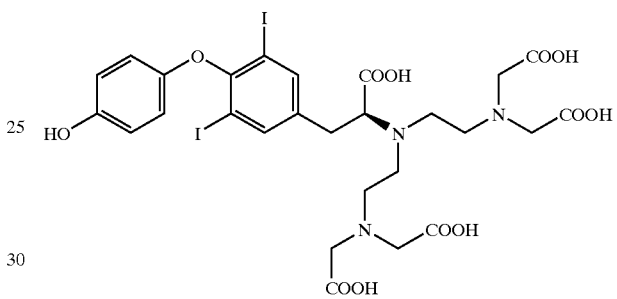

A suspension of the pentaester from the previous preparation (74.5 g; 69 mmol) in 0.25 M $H_2SO_4$ (1.65 L; 412 mmol) was stirred at 90° C. for 4 h. The resulting hot solution was filtered and then cooled to room temperature to yield a white suspension. The pH was adjusted to 13.5 by adding 10 M NaOH (150 mL, 1.5 mol) and the mixture was stirred at 20° C. for 5 h obtaining a clear solution. The pH was adjusted to 2.25 by adding 9 M $H_2SO_4$ and the resulting suspension was filtered to yield the free ligand (56 g; 67 mmol). Yield 97%.

mp: 178° C. (dec.); Acidic titer (0.1 M $HClO_4$): 102%; Complexometric titer (0.001 M $GdCl_3$): 99.7%; HPLC: 99% (area %)—Chromatographic method: Stationary phase: Lichrospher 100 RP-8 5 μm; 250×4 mm column packed by Merck KGaA; Temperature: 40° C.; Mobile phase: isocratic elution with premixed mobile phase is obtained by addition of n-octylamine (1 g) and 0.1 M EDTA disodium salt (10 mL) to a mixture of $CH_3CN$ (300 mL) and $H_2O$ (790 mL) buffering to pH 6 with $H_3PO_4$; Flow rate: 1 mL min$^{-1}$; Detection (UV): 245 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector, Merck KGaA. TLC: Rf 0.44; Stationary phase: Silica gel plates 60 $F_{254}$ Merck KGaA art 5715; Mobile phase: 4:4:2 $CHCl_3$:MeOH:25% aqueous $NH_4OH$; Detection: 1% $KMnO_4$ in 1 M NaOH; K.F.: 0.87%; $^{13}C$-NMR, $^1H$-NMR, MS and IR spectra were consistent with the structure. $[\alpha]^{20}$(c 2.48; 1 N NaOH ):

| λ (nm) | 589 | 578 | 546 | 436 |
|---|---|---|---|---|
| $[\alpha]^{20}_\lambda$ | −4.16° | −4.24° | −4.32° | −4.52° |

Elemental analysis (%):

|  | C | H | I | N | S |  |
|---|---|---|---|---|---|---|
| Calcd. | 38.45 | 3.71 | 30.09 | 4.98 | — |  |
| Found | 38.21 | 3.63 | 29.37 | 4.88 | <0.1 | anhydrous |

D) [[N,N-bis[2-[bis(Carboxymethyl)amino]ethyl]-O-(4-hydroxyphenyl)-3,5-diiodo-L-tyrosinate(5-)]gadolinate-(2-)]dihydrogen Compound with 1-Deoxy-1-(methylamino)-D-glucitol (1:2)

A 1 M solution of 1 deoxy-1-(methylamino)-D-glucitol (67.7 mL; 67.7 mmol) was added to a stirred suspension of the free ligand from the previous preparation (22 g; 25 mmol) in H$_2$O (600 mL), obtaining complete dissolution. A solution of GdCl$_3$.6H$_2$O (9.3 g; 25 mmol) in H$_2$O (20 mL) was then added dropwise maintaining the pH at 5.5 with 1 M 1 deoxy-1-(methylamino)-D-glucitol. The resulting solution was filtered over Millipore® (HAWP 0.45 μm) and loaded onto a column of Amberlite® XAD-1600 polystyrene resin (1 L). The resin was eluted with H$_2$O (3 L) and then with 95:5 H$_2$O:CH$_3$CN. The eluate was filtered over Millipore® (HAWP 0.45 μm), concentrated to 40 mL and, after adjusting the pH to 7.2 with 0.1 M HCl, was evaporated to dryness (1.3 kPa; 40° C.; P$_2$O$_5$) to yield the title compound (30.5 g; 21.9 mmol). Yield 87%.

mp: 193° C. (dec.); Free ligand (0.001 M GdCl$_3$):<0.1%; HPLC: 99% (area %) Chromatographic method: the same of previous step C); K.F.: 2.08%; MS spectrum was consistent with the structure. Elemental analysis (%):

|  | C | H | Gd | I | N |  |
|---|---|---|---|---|---|---|
| Calcd. | 35.48 | 4.50 | 11.33 | 18.29 | 5.05 |  |
| Found | 35.69 | 4.47 | 11.55 | 18.49 | 5.02 | anhydrous |

EXAMPLE 5

Preparation of the Two Compounds:

[[N,N-bis[2-[bis(carboxymethyl)amino]ethyl]-O-(4-hydroxy-3-iodophenyl)-3,5-diiodo-L-tyrosinate(5-)]gadolinate(2-)]dihydrogen compound with 1-deoxy-1-methyl-amino-D-glucitol (1:2)

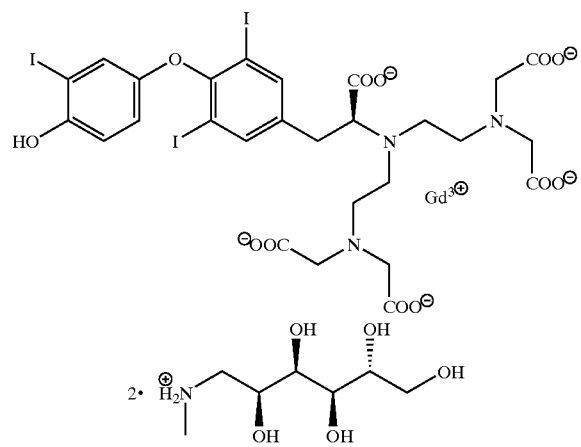

and

[[N,N-bis[2-[bis(carboxymethyl)amino]ethyl]-O-(4-hydroxy-3,5-diiodophenyl)-3,5-diiodo-L-tyrosinate (5-)]gadolinate(2-)]dihydrogen compound with 1-deoxy-1-methylamino-D-glucitol (1:2)

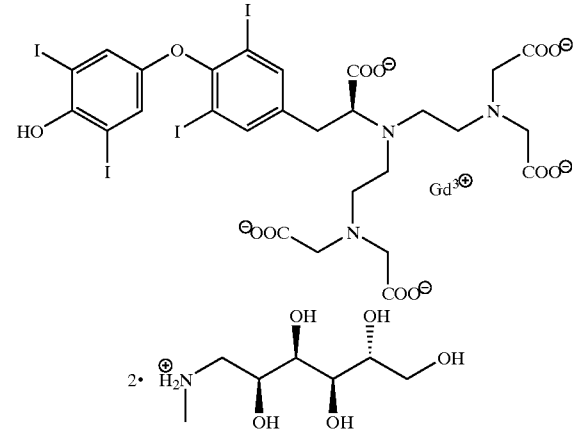

A) N,N-bis[2-[bis(Carboxymethyl)amino]ethyl]-O-(4-hydroxyphenyl)-3,5-diiodo-L-tyrosine (B 21920)

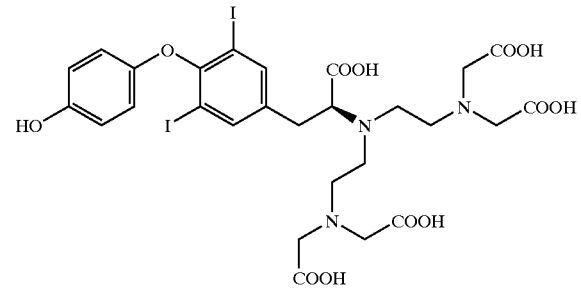

The compound was prepared according to Example 4.

B)

1) N,N-bis[2-[bis(carboxymethyl)amino]ethyl]-O-(4-hydroxy-3-iodophenyl)-3,5-diiodo-L-tyrosine

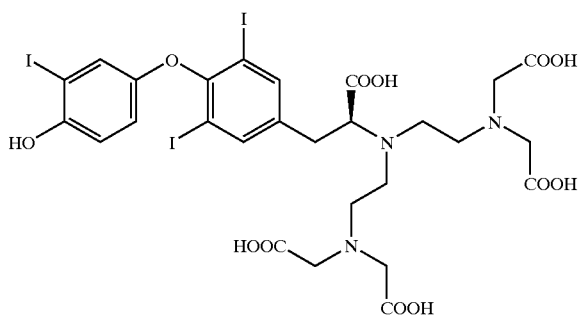

and

2) N,N-bis[2-[bis(carboxymethyl)amino]ethyl]-O-(4-hydroxy-3,5-diiodophenyl)-3,5-diiodo-L-tyrosine

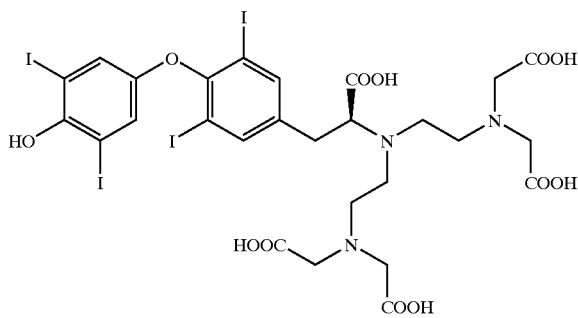

1 M NaOH (58.6 mL) was added at 20° C. to a suspension of N,N-bis[2-[bis(carboxymethyl)amino]ethyl]-O-(4-hydroxyphenyl)-3,5-diiodo-L-tyrosine (12.67 g; 15 mmol) in $H_2O$ (150 mL) until pH 10 was reached. A solution of $I_2$ (12.69 g; 50 mmol) and KI (21.58 g; 130 mmol) in $H_2O$ (100 mL) (47.7 mL; 23.7 mmol) was added dropwise to the resulting solution over 4.5 h, maintaining pH 10 by the addition of 1 M NaOH through a pH-stat apparatus. The mixture was filtered over Millipore® HA 0.45 m and acidified to pH 0 with 37% HCl (42 mL; 0.5 mol) to yield a precipitate that was filtered and dried (50° C.; 1.3 kPa; $P_2O_5$) (13.3 g). The solid was suspended in $H_2O$, then dissolved by adding 2 M NaOH up to pH 9 and acidified with 2 M HCl to pH 5, then it was purified by preparative HPLC:

Preparative Chromatographic method: Stationary phase: Lichroprep RP-8 25–40 μm; 250×50 mm column; Temperature: room temperature; Mobile phase: stepped gradient elution; A=0.01 M $KH_2PO_4$; B=0.01 M $KH_2PO_4$/$CH_3CN$ 8/2; C=$H_2O$/$CH_3CN$ 1/1;

| | Step timetable: | | | | |
|---|---|---|---|---|---|
| start (min) | end (min) | % A | % B | % C | flow rate (mL min$^{-1}$) |
| 0 | 15 | 100 | 0 | 0 | 60 |
| 15 | 92 | 0 | 100 | 0 | 60 |
| 92 | 110 | 0 | 0 | 100 | 60 |
| 110 | 130 | 100 | 0 | 0 | 60 |

Detection (UV): 210 nm; UV detector attenuation: 256; Injection: 100 mL; Sample concentration: 10 mg mL$^{-1}$; Instrumentation: Merck KGaA Prepbar 100;

The two crude ligands were separately suspended in water (250 mL) and dissolved by the addition of 10 M NaOH up to pH 6. Acidification of the two solutions to pH 2.5 with 37% HCl led to formation of two precipitates which were filtered and dried (50° C.; 1.3 kPa; $P_2O_5$) to yield the product (B1) (3,1 g; 3.2 mmol; yield 21%) and (B2) (2.7 g; 2.5 mmol; yield 17%).

COMPOUND B1:

mp: 188° C. (dec.); Acidic titer (0.1 N $HClO_4$):95.5%; Complexometric titer (0.001 M $GdCl_3$): 96.6%; HPLC: 99% (area %) Chromatographic method: the same of Ex. 4, step A); K.F.: 3.84%; $^{13}$C-NMR, $^1$H-NMR and MS spectra were consistent with the structure. Elemental analysis (%):

| | C | H | I | N | |
|---|---|---|---|---|---|
| Calcd. | 33.36 | 3.12 | 39.28 | 4.34 | |
| Found | 33.34 | 2.91 | 39.14 | 4.33 | anhydrous |

COMPOUND B2:

mp: 194° C. (dec.); Complexometric titer (0.001 M $GdCl_3$): 96.4%; HPLC: 98.6 (area %) Chromatographic method: the same of Ex. 4, step A); K.F.: 3.07%; $^{13}$C-NMR, $^1$H-NMR and MS spectra were consistent with the structure. Elemental analysis (%):

| | C | H | I | N | |
|---|---|---|---|---|---|
| Calcd. | 29.31 | 2.67 | 46.35 | 3.84 | |
| Found | 29.31 | 2.57 | 45.33 | 3.78 | anhydrous |

C1) [[N,N-bis[2-[bis(Carboxymethyl)amino]ethyl]-O-(4-hydroxy-3-iodophenyl)-3,5-diiodo-L-tyrosinate(5-)]gadolinate(2-)]dihydrogen Compound with 1-Deoxy-1-methylamino-D-glucitol (1:2)

A 1 M aqueous solution of 1-deoxy-1-methylamino-D-glucitol (5.4 mL; 5.4 mmol) was dropped into a suspension of compound B1 (B 22090) (1.94 g; 2 mmol) in $H_2O$ (100 mL), stirring until complete dissolution. A 0.33 M solution of $GdCl_3$ (6.2 mL; 2.05 mmol) was slowly added, maintaining the pH of the mixture at 6.5 by addition of a 1 M aqueous solution of 1-deoxy-1-methylamino-D-glucitol through a pH-stat apparatus. After stirring for 1 h at room temperature the cloudy solution was filtered over Millipore® HA 0.45 m. The solution was loaded onto a column of Amberlite® XAD 16-00 polystyrene resin (200 mL) and the column eluted with $H_2O$ (1 L) followed by 3/1 $H_2O$/$CH_3CN$ mixture (1 L). The fractions containing the complex were combined and concentrated to 150 mL. The resulting solution was filtered over Millipore® HA 0.45 m and evaporated to dryness to give the title compound (2.2 g; 1.45 mmol). Yield 76%.

mp: 163° C. (dec.); Free ligand (0.001 M $GdCl_3$):<0.1%; HPLC: 99.2 (area %)—Chromatographic method: Stationary phase: Lichrospher 100 RP-8 5 μm; 250×4 mm column packed by Merck KGaA; Temperature: 40° C.; Mobile phase: isocratic elution with premixed mobile phase: 1 g of n-octylamine is added to 350 mL of acetonitrile mixed with 650 mL of water. The solution is buffered to pH 6 with $H_3PO_4$; Flow rate: 1 mL min$^{-1}$; Detection (UV): 210 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector. K.F.: 4.18%; Elemental analysis (%):

| | C | H | Gd | I | N | |
|---|---|---|---|---|---|---|
| Calcd. | 32.53 | 4.06 | 10.39 | 25.14 | 4.63 | |
| Found | 32.45 | 4.00 | 10.38 | 25.01 | 4.59 | anhydrous |

C2) [[N,N-bis[2-[bis(Carboxymethyl)amino]ethyl]-O-(4-hydroxy-3,5-diiodophenyl)-3,5-diiodo-L-tyrosinate(5-)]gadolinate(2-)]dihydrogen Compound with 1-Deoxy-1-methylamino-D-glucitol (1:2)

A 1 M aqueous solution of 1-deoxy-1-methylamino-D-glucitol (4.6 mL; 4.6 mmol) was dropped into a suspension of compound B2 (1.53 g; 1.4 mmol) in $H_2O$ (100 mL), stirring until complete dissolution. A 0.33 M solution of $GdCl_3$ (4.2 mL; 2.05 mmol) was slowly added, maintaining the pH of the mixture at 6.5 by addition of a 1 M aqueous solution of 1-deoxy-1-methylamino-D-glucitol through a pH-stat apparatus. After stirring for 1 h at room temperature the solution was filtered over Millipore® HA 0.45 m and loaded onto a column of Amberlite® XAD 16-00 polystyrene resin (200 mL); the column was eluted with $H_2O$ (1 L) followed by 3/1 $H_2O/CH_3CN$ mixture (1 L). The fractions containing the complex were combined and, after concentration to 150 mL, filtered over Millipore® HA 0.45 m. The solution was evaporated to dryness to give the title compound (1.85 g; 1.13 mmol). Yield 81%.

mp: 153° C. (dec.); Free ligand (0.001 M $GdCl_3$):<0.1%; HPLC: 98.8 (area %) Chromatographic method: the same of previous step C1); K.F.: 1.73%; Elemental analysis (%):

| | C | H | Gd | I | N | |
|---|---|---|---|---|---|---|
| Calcd. | 30.03 | 3.69 | 9.59 | 30.96 | 4.27 | |
| Found | 29.78 | 3.81 | 9.43 | 30.59 | 4.21 | anhydrous |

EXAMPLE 6

[[N,N-bis[2-[bis(Carboxymethyl)amino]ethyl]-O-(4-hydroxyphenyl)-L-tyrosinate(5-)]gadolinate(2-)] dihydrogen Compound with 1-Deoxy-1-methylamino-D-glucitol (1:2)

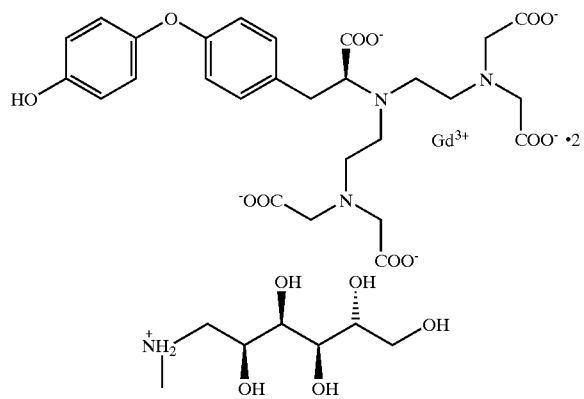

A) N,N-bis[2-[bis(Carboxymethyl)amino]ethyl]-O-(4-hydroxyphenyl)-3,5-diiodo-L-tyrosine

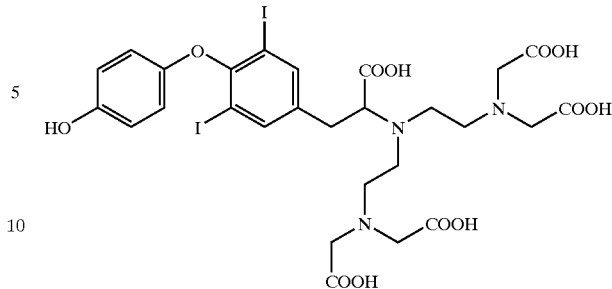

The compound was prepared according to Example 4.

B) N,N-bis[2-[bis(Carboxymethyl)amino]ethyl]-O-(4-hydroxyphenyl)-L-tyrosine

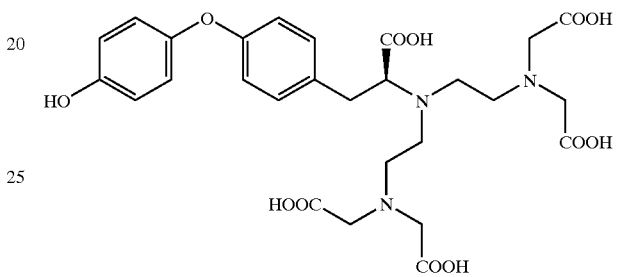

To a suspension of N,N-bis[2-[bis(carboxymethyl)amino]ethyl]-O-(4-hydroxyphenyl)-3,5-diiodo-L-tyrosine (5,1 g; 6 mmol) 1 M NaOH (15 mL; 15 mmol) was added until pH 7 then Pd on carbon (3 g) was added. The suspension was stirred over 90 min under a hydrogen atmosphere (consumed H2 300 mL; 12.2 mmol) at 26° C. and atmospheric pressure, maintaining pH 7 by the addition of 1 M NaOH (11.33 mL; 11.33 mmol) through a pH-stat apparatus. The suspension was filtered over Millipore® HA 0.45 m and 6 M HCl (7 mL; 42 mmol) was added to the solution down to pH 0.5, then the mixture was loaded onto a column of Amberlite® XAD 16-00 polystyrene resin (1 L). The column was eluted with $H_2O$ until I- ions were not detectable in the eluate any more, then washed with 2% aqueous $NaHSO_3$ (100 mL) and $H_2O$ (2 L); elution with 8/2 $H_2O/CH_3CN$ afforded the product. After evaporation of the solvent the amorphous residue was suspended in $CH_3CN$ and the solvent evaporated. Such procedure was repeated until the desired compound was recovered by filtration (3.07 g; 5.2 mmol). Yield 86%.

mp: 134° C. (dec.); Acidic titer (0.1 N $HClO_4$): 100.5%; Acidic titer (0.1 N NaOH): 97.3%; Complexometric titer (0.1 N $ZnSO_4$): 96%; TLC: Rf 0.3; Stationary phase: Silica gel plates 60 $F_{254}$ Merck KGaA art 5715; Mobile phase: 4/4/2 $CHCl_3/CH_3OH/25\%$ aqueous $NH_4OH$; Detection: 1% $KMnO_4$ in 1 M NaOH; HPLC: 99.5 (area %) Chromatographic method: the same of Ex.4, A); K.F.: 1.38%; $^{13}$C-NMR, $^1$H-NMR, MS and IR spectra were consistent with the structure. Elemental analysis (%):

| | C | H | N | I | |
|---|---|---|---|---|---|
| Calcd. | 54.82 | 5.62 | 7.10 | — | |
| Found | 54.17 | 5.62 | 7.57 | <0.1 | anhydrous |

$[\alpha]^{20}$(c 2.55; 0.1 N NaOH):

| λ (nm) | 589 | 578 | 543 | 436 | 405 | 365 |
|---|---|---|---|---|---|---|
| $[\alpha]^{20}_\lambda$ | −3.13° | −3.17° | −3.53° | −5.95° | −6.42° | −7.17° |

C) [N,N-bis[2-[bis(Carboxymethyl)amino]ethyl]-O-(4-hydroyphenyl)-L-tyrosinate(5-)]gadolinate(2-)]dihydrogen Compound with 1-Deoxy-1-methylamino-D-glucitol (1:2)

A 1 M aqueous solution of 1-deoxy-1-methylamino-D-glucitol (25 mL; 25 mmol) was dropped into a suspension of the product from the previous preparation (5.32 g; 9 mmol) in H₂O (200 mL), stirring until complete dissolution. A 0.4 M solution of GdCl₃ (22 mL; 8.8 mmol) was slowly added, maintaining the pH of the mixture at 6.5 by addition of a 1 M aqueous solution of 1-deoxy-1-methylamino-D-glucitol. After stirring for 1 h at room temperature the solution was filtered over Millipore® HA 0.45 m. The solution was loaded onto a column of Amberlite® XAD 16-00 polystyrene resin (300 mL) and the column eluted with water followed by 9/1 H₂O/CH₃CN mixture. The fractions containing the complex were combined and, after concentration to 150 mL, filtered over Millipore® HA 0.45 m. The solution was evaporated to dryness to give the title compound as a white solid (7.79 g; 6.8 mmol). Yield 76%.

mp: 125° C. (dec.); Free ligand (0.001 M GdCl₃):<0.1%; HPLC: 99.9 (area %)—Chromatographic method: Stationary phase: Lichrospher 100 RP-8 5 μm; 250×4 mm column packed by Merck KGaA; Temperature: 40° C.; Mobile phase: isocratic elution with premixed mobile phase: 1 g of n-octylamine is added to 230 mL of acetonitrile mixed with 770 mL of water. The solution is buffered to pH 6 with H₃PO₄; Flow rate: 1 mL min⁻¹; Detection (UV): 210 nm; Injection: 10 μL; Sample concentration: 1 mg mL⁻¹; Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 4000 UV detector. K.F.: 2.98%; MS spectrum was consistent with the structure. Elemental analysis (%):

|  | C | H | N | Gd |  |
|---|---|---|---|---|---|
| Calcd. | 43.34 | 5.68 | 6.16 | 13.84 |  |
| Found | 43.50 | 5.72 | 6.15 | 13.89 | anhydrous |

EXAMPLE 7

[[N²,N²-bis[2-[bis(Carboxymethyl)amino]ethyl]-N,N-[bis(phenylmethyl)]-L-glutaminate(5-)]gadolinate(2-)]dihydrogen Compound with 1-Deoxy-1-methylamino-D-glucitol (1:2)

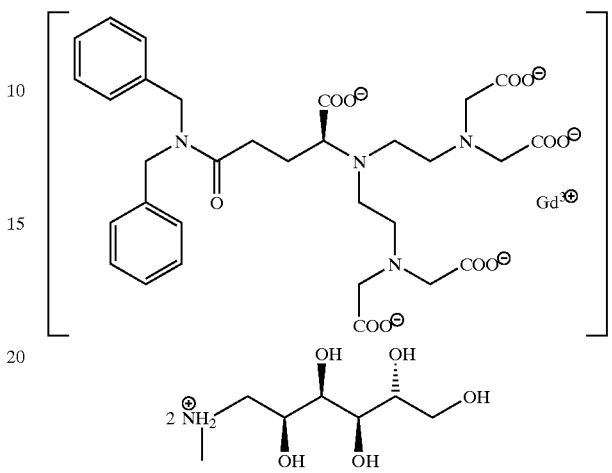

A) N²-[(Phenylmethoxy)carbonyl]-N,N-[bis(phenylmethyl)]L-glutamine Methyl Ester

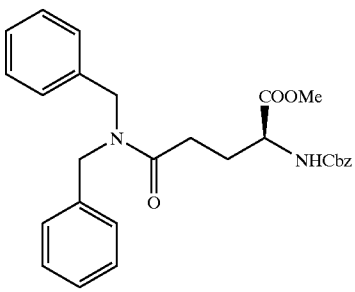

To a stirred solution of (S)-5-oxo-3-[(phenylmethoxy)carbonyl]-4-oxazolidinepropanoyl chloride, prepared according to Example 3, (33.3 g; 107 mmol) in CHCl₃ (250 mL) dibenzylamine was added dropwise (214 mmol; 42.2 g; 41 mL). The resulting mixture was filtered, the solution concentrated to 90 mL and again filtered. The clear solution was evaporated under reduced pressure (2 kPa) to provide (S)-5-oxo-4-[3-oxo-3-[bis(phenylmethyl)amino]propyl]-3-oxazolidinecarboxylic acid phenylmethyl ester (50.6 g; 107 mmol), that was not isolated. This intermediate was dissolved in MeOH (300 mL) and the resulting solution was added dropwise with a 1 M solution of MeONa (110 mmol; 110 mL) in MeOH. The resulting mixture was concentrated to 200 mL under reduced pressure (2 kPa) and then added to a stirred mixture of 1 M HCl (150 mL) and EtOAc (300 mL). The organic phase was washed with 1 M HCl (200 mL), dried (Na₂SO₄) and concentrated (2 kPa) to dryness. The crude (49 g) was purified by flash chromatography (Stationary phase: Silica gel 230–400 mesh Merck KGaA art 9385 (1 Kg). Mobile phase: 7:3 n-hexane:EtOAc (10 L)) to give the desired product (40 g; 84.3 mmol). Overall yield 79%.

TLC: Rf 0.25; Stationary phase: Silica gel plates 60 $F_{254}$ Merck KGaA art 5715; Mobile phase: 6:4 n-hexane:EtOAc; Detection: 1% $KMnO_4$ in 1 M NaOH; HPLC: 99.7% (area %) Chromatographic method: the same of Ex. 3, Step A); $^{13}C$-NMR, $^1H$-NMR and MS spectra were consistent with the structure.

B) N,N-[bis(Phenylmethyl)]-L-glutamine Methyl Ester

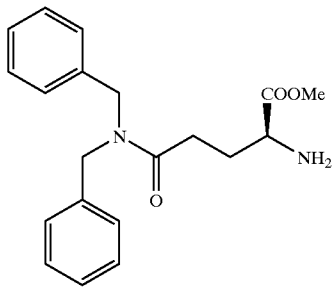

To a stirred suspension of the protected derivative from the previous preparation (38.2 g; 80 mmol) in acetic acid (80 mL) 33% HBr in acetic acid was slowly added (75 mL; 412 mmol) and the mixture was stirred until the gas evolution was over. The mixture was then carefully poured into $H_2O$ (500 mL), adjusting the pH of the resulting mixture to 2 by the addition of 2 M NaOH. The solution was extracted with EtOAc (3×200 mL). The pH of the aqueous phase was adjusted to 7 by adding 2 M NaOH and the mixture was extracted with EtOAc (2×150 mL) to give a first solution containing the reaction product. The organic layers relative to the first extraction were extracted with 1 M HCl (3×200 mL). The aqueous phases were combined, the pH adjusted to 7.4 by adding 10 M NaOH and the resulting mixture extracted with EtOAc (3×200 mL) to yield a second solution of the reaction product. The two solutions were combined, dried ($Na_2SO_4$) and concentrated under reduced pressure (2 kPa) to give the desired amino ester derivative (23 g; 67.6 mmol). Yield 85%.

TLC: Rf 0.68; Stationary phase: Silica gel plates 60 $F_{254}$ Merck KGaA art 5715; Mobile phase: 8:2 $CH_2Cl_2$/MeOH; Detection: 1% $KMnO_4$ in 1 M NaOH; HPLC: 98% (area %) Chromatographic method: the same of Ex. 3, Step A); $^{13}C$-NMR and $^1H$-NMR spectra were consistent with the structure.

C) $N^2,N^2$-bis[2-[bis[2-(1,1-Dimethylethoxy)-2-oxoethyl]amino]ethyl]-N,N-[bis(phenylmethyl)]-L-glutamine Methyl Ester

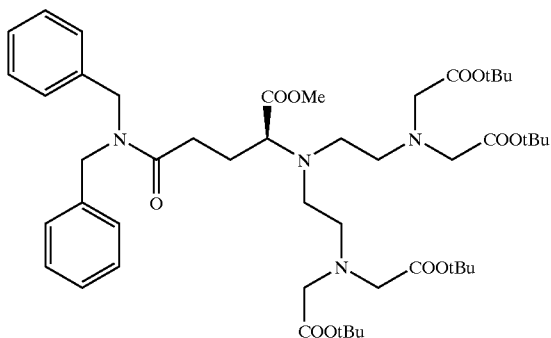

A 2 M pH 8 phosphate buffer (600 mL) was added to a solution of N-(2-bromoethyl)-N-[2-(1,1-dimethylethoxy)-2-oxoethyl]glycine 1,1-dimethylethyl ester (45.6 g; 135 mmol) (prepared according to Example 1) and of the compound from the previous preparation (22 g; 64.5 mmol) in $CH_3CN$ (500 mL). After 24 h of vigorous stirring the two phases were separated and the organic phase was evaporated under reduced pressure (2 kPa). The residue was dissolved in $CH_2Cl_2$ (300 mL). The resulting solution was washed with water (200 mL), dried ($Na_2SO_4$) and concentrated to dryness. The crude was purified by flash chromatography (Stationary phase: Silica gel 230–400 mesh Merck KGaA art 9385 (1000 g). Mobile phase: 7:3 n-hexane:EtOAc (10 L)) to give the desired compound (40.7 g, 46 mmol). Yield 71%.

HPLC: 98.6% (area %) Chromatographic method: the same of Ex. 3, Step A); TLC: Rf 0.7; Stationary phase: Silica gel plates 60 $F_{254}$ Merck KGaA art 5715; Mobile phase: 6:4 n-hexane:EtOAc; Detection: 1% $KMnO_4$ in 1 M NaOH; $^{13}C$-NMR, $^1H$-NMR and MS spectra were consistent with the structure.

D) $N^2,N^2$-bis[2-[bis(Carboxymethyl)amino]ethyl]-N,N-[bis(phenylmethyl)]-L-glutamine

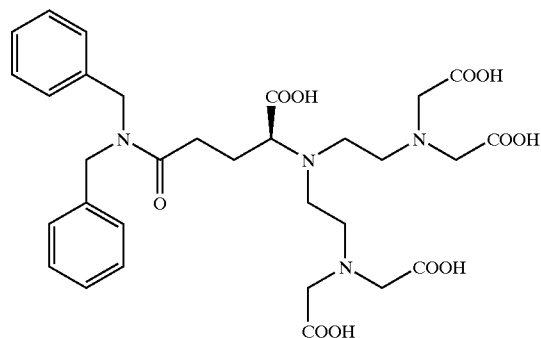

0.5 M $H_2SO_4$ (500 mL; 250 mmol) was added to a suspension of the pentaester from the previous preparation (40.6 g; 46 mmol) in $H_2O$ (400 mL); the resulting mixture was stirred at 60° C. for 8 h, then at 90° C. for 2 h. After cooling to r.t. the pH was adjusted to 13.5 by adding 10 M NaOH. After stirring for 2 h the pH of the mixture was adjusted to 6.0 by adding 98% $H_2SO_4$ and the clear solution was concentrated to a final volume of 200 mL. The pH was adjusted to 2 adding 98% $H_2SO_4$; then $CH_3CN$ (30 mL) was added. The mixture was loaded onto a column of Amberlite® XAD 1600 polystyrene resin (1.5 L) conditioned with 7:1 $H_2O/CH_3CN$. The product was recovered by increasing the ratio of $CH_3CN$ in the eluting mixture from 7:1 $H_2O/CH_3CN$ to 1:1 $H_2O/CH_3CN$. The free ligand was obtained (18.5 g; 28.8 mmol). Yield 62%.

m.p.: 116° C.; HPLC: 99% (area %) Chromatographic method: the same of Ex. 3, Step A); $^3C$-NMR, $^1H$-NMR and MS spectra were consistent with the structure. $[\alpha]^{20}$(c 4.0, 0.1 M NaOH);

| λ (nm) | 589 | 578 | 546 | 436 | 405 | 365 |
|---|---|---|---|---|---|---|
| $[\alpha]^{20}_\lambda$ | +1.00° | +0.75° | +0.85° | +1.15° | +1.20° | +1.37° |

Elemental analysis (%):

| | C | H | N |
|---|---|---|---|
| calcd. | 57.76 | 6.25 | 8.69 |

|        | C     | H    | N    |           |
|--------|-------|------|------|-----------|
| found  | 57.62 | 6.05 | 9.05 | anhydrous |

E) [[N²,N²-bis[2-[bis(Carboxymethyl)amino]ethyl]-N,N-[bis(phenylmethyl)]-L-glutaminate(5-)]gadolinate(2-)] dihydrogen Compound with 1-Deoxy-1-methylamino-D-glucitol (1:2)

A 1 M solution of 1-deoxy-1-(methylamino)-D-glucitol (87 mL; 87 mmol) was dropped into a suspension of the compound from the previous preparation (16.4 g; 25.5 mmol) in H₂O (350 mL), stirring until complete dissolution. A 0.482 M solution of GdCl₃ (52.9 mL; 25.5 mmol) was slowly added, maintaining the pH of the mixture at 6.5 by addition of a 0.5 M solution of 1-deoxy-1-(methylamino)-D-glucitol. After stirring for 1 h at room temperature the solution was concentrated (2 kPa; final volume 200 mL; pH 6.17). The mixture was loaded onto a column of Amberlite® XAD 1600 polystyrene resin (1500 mL) and the column eluted with water followed by 3:7 CH₃CN/H₂O mixture, The fractions containing the complex were combined and, after concentration, the resulting cloudy solution was filtered over Millipore® HA-0.22 æm. After adjusting the pH to 6.96 adding a 0.08 M solution of 1-deoxy-1-methylamino-D-glucitol the solution was evaporated to dryness to give the title compound (27.55 g; 23.2 mmol). Yield 91%.

m.p.: 125° C.; HPLC: 99.7% (area %)–Chromatographic method: Stationary phase: Lichrospher 100 RP-8 5 μm; 250×4 mm column packed by Merck KGaA; Temperature: 40° C.; Mobile phase: isocratic elution with premixed mobile phase: 1 g of n-octylamine is added to 270 mL of acetonitrile mixed with 730 mL of water and 2 mL of 0.1 M EDTA. The solution is buffered to pH 6 with H₃PO₄; Flow rate: 1 mL min⁻¹; Detection (UV): 210 nm; Injection: 10 μL; Sample concentration: 1 mg ML⁻¹; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA. Free ligand (0.001 M GdCl₃):<0.1%; MS spectrum was consistent with the structure. Elemental analysis (%):

|        | C     | H    | N    | Gd    |           |
|--------|-------|------|------|-------|-----------|
| Calcd. | 45.44 | 6.03 | 7.06 | 13.22 |           |
| Found  | 45.40 | 6.16 | 6.94 | 13.10 | anhydrous |

With analogous synthetic method, starting from (S)-5-oxo-3-[(phenylmethoxy)carbonyl]-4-oxazolidinepropanoyl chloride (prepared according to Example 3) and dicyclohexylamine (commercial product), the following ligand and its gadolinium chelate were obtained:

N²,N²-bis[2-[bis(carboxymethyl)amino]ethyl]-N,N-[dicyclohexyl]-L-glutamine

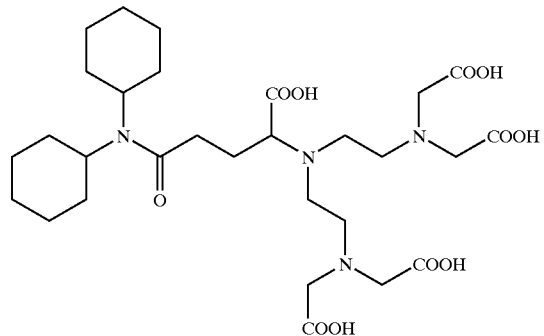

and

[[N²,N²-bis[2-[bis(carboxymethyl)amino]ethyl]-N,N-[dicyclohexyl]-L-glutaminato(5-)]gadolinate(2-)] dihydrogen compound with 1-deoxy-1-methylamino-D-glucitol (1:2)

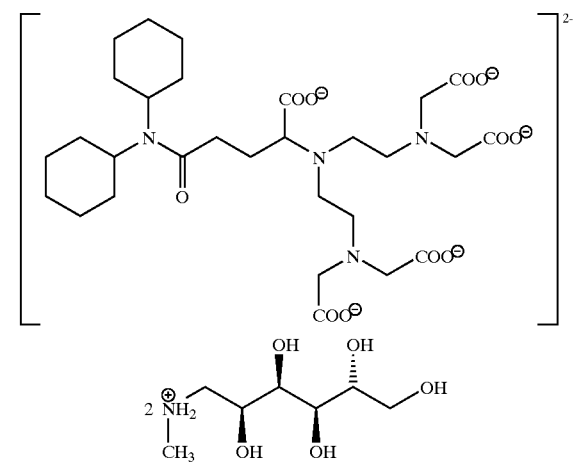

With analogous synthetic method, the following ligand and its gadolinium chelate were obtained:

[4-carboxy-4-[bis[2-[bis(carboxymethyl)amino]-ethyl]-amino]-1-oxobutyl]-L-tryptophane

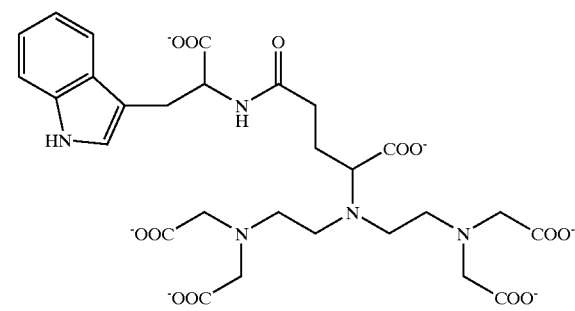

and

[[N-[4-carboxy-4-[bis[2-[bis(carboxymethyl)amino]-ethyl]amino]-1-oxobutyl]-L-tryptophanate(6-)] gadolinate(3-)]trisodium salt

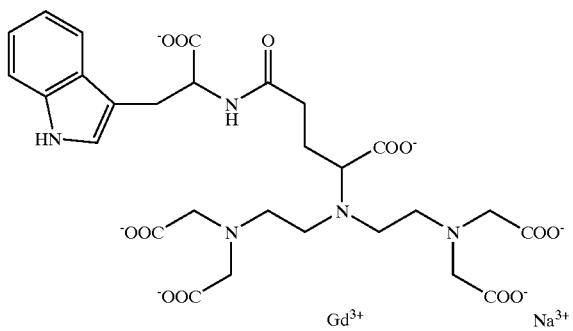

EXAMPLE 8

[[N²,N²-bis[2-[bis(Carboxymethyl)amino]ethyl]-N⁶-(diphenylacetyl)-L-lysinate(5-)]gadolinate(2-)] dihydrogen Compound with 1-Deoxy-1-methylamino-D-glucitol (1:2)

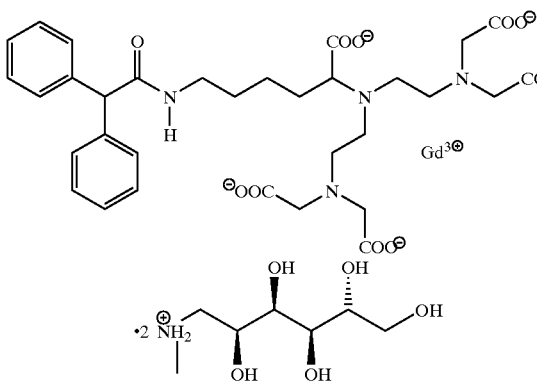

A) N²,N²-bis[2-[bis[2-(1,1-Dimethylethoxy)-2-oxoethyl]amino]ethyl]-N⁶-(diphenylacetyl)-L-lysine1,1-dimethylethyl Ester

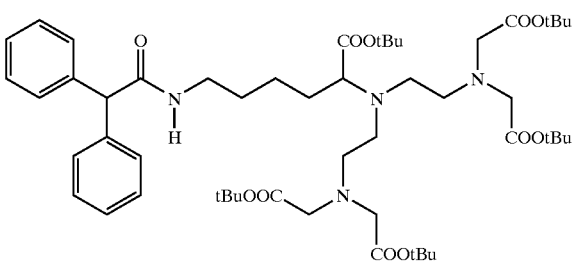

A solution of α-(phenyl)benzeneacetyl chloride (3.46 g; 15 mmol) (commercial product), in CHCl₃ (75 mL) was dropped into a solution of N²,N²-bis[2-[bis[2-(1,1-dimethylethoxy)-2-oxoethyl]amino]ethyl]-L-lysine1,1 dimethylethyl ester, prepared according to Example 2, (11.17 g; 15 mmol) in CHCl₃ (190 mL), maintaining the mixture at 5÷10° C. The resulting solution was washed with a saturated aq solution of NaHCO₃ (3×100 mL); the organic phase was dried over Na₂SO₄ and concentrated to dryness to yield an oil (18 g) which was purified by flash chromatography:

Column:=100 mm; h=250 mm; Stationary phase: Silica gel 230–400 mesh Merck KGaA art 9385 (1 kg); Mobile phase: 7/3 n-hexane/EtOAc; The desired product was obtained (12.2 g; 13 mmol). Yield 87%. Acidic titer (0.1 N HClO₄): 104.4%; TLC: Rf 0.21; Stationary phase: Silica gel plates 60 $F_{254}$ Merck KGaA art 5715; Mobile phase: 7/3 n-hexane/EtOAc; Detection: 1% KMnO₄ in 1 M NaOH; HPLC: 99.7% (area %) Chromatographic method: Stationary phase: Lichrosorb RP-Select B 5 μm; 250×4 mm column packed by Merck KGaA; Temperature: 45° C.; Mobile phase: gradient elution; A=0.01 M KH₂PO₄ and 0.017 M H₃PO₄ in water; B=CH₃CN;

| Gradient timetable: | min | % A | % B |
|---|---|---|---|
| | 0 | 95 | 5 |
| | 30 | 20 | 80 |
| | 45 | 20 | 80 |

Flow rate: 1 mL min⁻¹; Detection (UV): 210 nm, 280 nm; Injection: 10 μL; Sample concentration: 1 mg mL⁻¹; Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 4000 UV detector. $^{13}$C-NMR, $^{1}$H-NMR, MS and IR spectra were consistent with the structure. Elemental analysis (%):

| | C | H | N |
|---|---|---|---|
| Calcd. | 66.50 | 8.80 | 5.97 |
| Found | 65.99 | 8.89 | 5.76 |

$[\alpha]^{20}$(c 5.00; CHCl₃):

| λ (nm) | 589 | 578 | 546 | 436 | 405 | 365 |
|---|---|---|---|---|---|---|
| $[\alpha]^{20}_\lambda$ | −22.30° | −24.02° | −27.52° | −49.68° | −41.64° | −86.00° |

B) N²,N²-bis[2-[bis(Carboxymethyl)amino]ethyl]-N⁶-(diphenylacetyl)-L-lysine

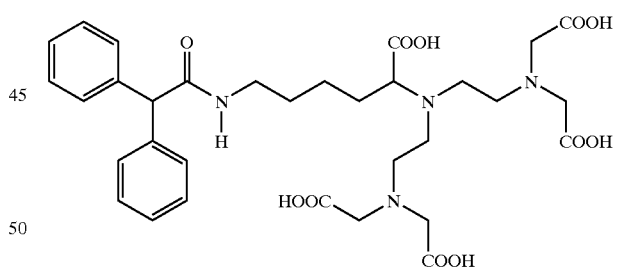

A solution of the pentaester from the previous preparation (10.7 g; 11.4 mmol) in CF₃COOH (150 mL; 1.95 mol) was stirred over 18 h under N₂ atmosphere. After evaporation (40° C.; 2 kPa) the residue was dissolved in CH₂Cl₂ (3×100 mL) evaporating the solvent each time (40° C.; 2 kPa). The crude was dissolved in a 9/1 H₂O/CH₃CN mixture and the solution was loaded onto a column of Amberlite® XAD 16-00 polystyrene resin. The column was eluted with H₂O (1.5 L), then with 4/1 H₂O/CH₃CN, obtaining the product. After concentration to 120 mL the resulting solution was filtered over Millipore® HA 0.45 m and evaporated. The amorphous residue was suspended in CH₃CN and the solvent evaporated. Such procedure was repeated until the desired product was recovered by filtration (5.83 g; 8.9 mmol). Yield 78%.

mp: 124° C. (dec.); Acidic titer (0.1 N NaOH): 101.1%; Acidic titer (0.1 N HClO$_4$): 97.4%; Complexometric titer (0.1 N GdCl$_3$): 96.7%; TLC: Rf 0.36; Stationary phase: Silica gel plates 60 F$_{254}$ Merck KGaA art 5715; Mobile phase: 4/4/2 CHCl$_3$/CH$_3$OH/25% aq NH$_4$OH; Detection: 1% KMnO$_4$ in 1 M NaOH; HPLC: 99.9% (area %) Chromatographic method: the same of previous Step A); K.F.: 1.08%; $^{13}$C-NMR, $^1$H-NMR, MS and IR spectra were consistent with the structure. Elemental analysis (%):

|  | C | H | N |  |
|---|---|---|---|---|
| Calcd. | 58.34 | 6.43 | 8.51 |  |
| Found | 57.92 | 6.45 | 8.66 | anhydrous |

$[\alpha]^{20}$(c 2.51; 0.1 M NaOH):

| λ (nm) | 589 | 578 | 546 | 436 | 405 | 365 |
|---|---|---|---|---|---|---|
| $[\alpha]^{20}{}_\lambda$ | −5.97° | −8.32° | −10.27° | −17.91° | −21.26° | −25.12° |

C) [[N$^2$,N$^2$-bis[2-[bis(Carboxymethyl)amino]ethyl]-N$^6$-(diphenylacetyl)-L-lysinate(5-)]gadolinate(2-)]dihydrogen Compound with 1-Deoxy-1-methylamino-D-glucitol (1:2)

A 1 M aq solution of 1-deoxy-1-methylamino-D-glucitol (17.3 mL; 17.3 mmol) was dropped into a stirred suspension of the free ligand from the previous preparation (3.95 g; 6 mmol) in H$_2$O (150 mL) to give a clear solution. A 0.4 M solution of GdCl$_3$ (14.5 mL; 5.8 mmol) was slowly added, maintaining the pH of the mixture at 6.5 by addition of a 1 M aq solution of 1-deoxy-1-methylamino-D-glucitol. After stirring for 1 h at room temperature the solution was filtered over Millipore® HA 0.45 m and loaded onto a column of Amberlite® XAD 16-00 polystyrene resin (300 mL). The column was eluted with water followed by 9/1 H$_2$O/CH$_3$CN mixture. The fractions containing the complex were combined and, after concentration to 150 mL, the resulting solution was filtered over Millipore® HA 0.45 m. The solution was evaporated to dryness to give the title compound (6.2 g; 5.2 mmol). Yield 86%.

mp: 127° C. (dec.); Free ligand (0.001 M GdCl$_3$):<0.1%; HPLC: 99.9% (area %) Chromatographic method: Stationary phase: Lichrospher 100 RP-8 5 μm; 250×4 mm column packed by Merck KGaA; Temperature: 40° C.; Mobile phase: isocratic elution with premixed mobile phase: 1 g of n-octylamine is added to 280 mL of acetonitrile mixed with 720 mL of water and 2 mL of 0.1 M EDTA. The solution is buffered to pH 6 with H$_3$PO$_4$; Flow rate: 1 mL min$^{-1}$; Detection (UV): 210 nm; Injection: 10 μL; Sample concentration: 1 mg mL$^{-1}$; Instrumentation: Merck KGaA—Hitachi L 6200 low pressure gradient pump, Merck KGaA—Hitachi AS 2000 autosampler, Merck KGaA T6300 column thermostat, Merck KGaA—Hitachi L 4000 UV detector. K.F.: 2.28%; MS spectrum was consistent with the structure. Elemental analysis (%):

|  | C | H | N | Gd | Cl |  |
|---|---|---|---|---|---|---|
| Calcd. | 45.91 | 6.11 | 6.98 | 13.07 | — |  |
| Found | 46.30 | 6.24 | 7.08 | 13.09 | <0.1 | anhydrous |

With analogous synthetic method, starting from N$^2$,N$^2$-bis[2-[bis[2-(1,1-dimethylethoxy)-2-oxoethyl]amino]-ethyl]-L-lysine1,1-dimethylethyl ester, prepared according to Example 2, and, -(diphenyl)benzeneacetyl chloride, prepared from the corresponding commercially available triphenylacetic acid [C.A.S. 595-91-5] with standard procedure, the following ligand and his gadolinium chelate were obtained:

N$^2$,N$^2$-Bis[2-[bis(carboxymethyl)amino]ethyl]-N$^6$-(triphenylacetyl)-L-lysine

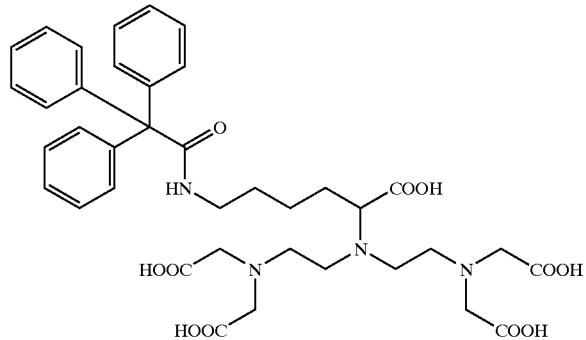

and

[[N$^2$,N$^2$-bis[2-[bis(carboxymethyl)amino]ethyl]-N$^6$-(triphenylacetyl)-L-lysinate(5-)]gadolinate(2-)] dihydrogen compound with 1-deoxy-1-methylamino-D-glucitol (1:2).

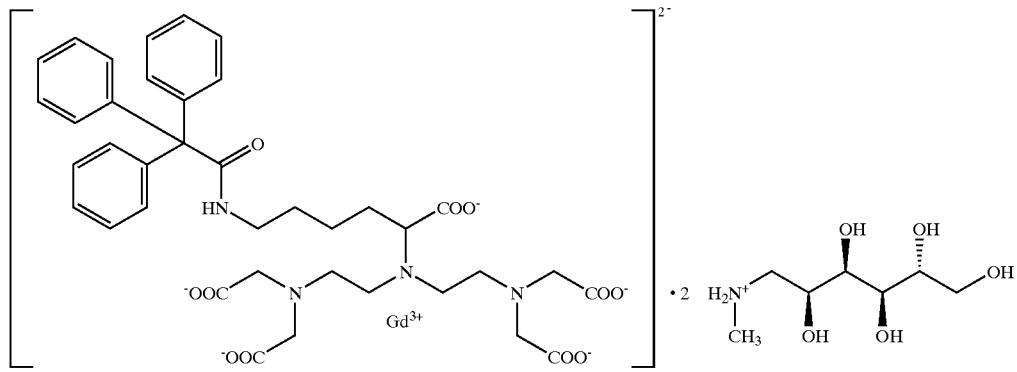

EXAMPLE 9

[[N²,N²-bis[2-[bis(carboxymethyl)amino]ethyl]-N⁶-(dicyclohexylacetyl)-L-lysinate(5-)]gadolinate(2-)] dihydrogen compound with 1-deoxy-1-methylamino-D-glucitol (1:2)

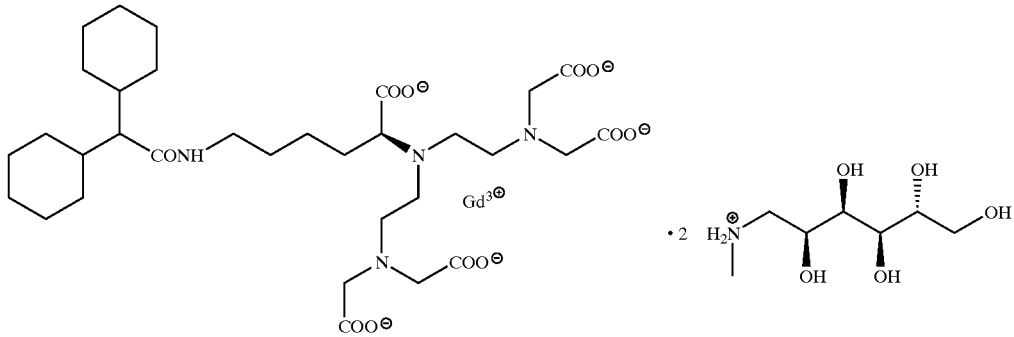

A) N²,N²-bis[2-[bis[2-(1,1-Dimethylethoxy)-2-oxo-ethyl]amino]ethyl]-N⁶-(dicyclohexylacetyl)-L-lysine 1,1-dimethylethyl Ester

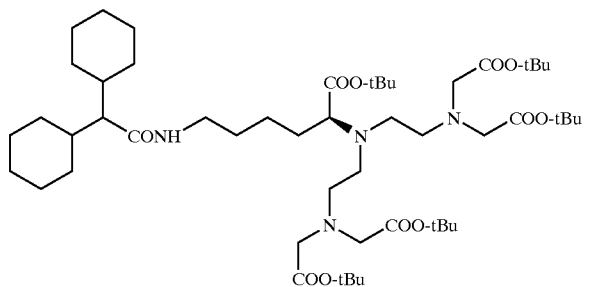

A solution of α-(cyclohexyl)cyclohexylacetic acid (commercial product) (3.36 g; 15 mmol) in SOCl₂ (3.2 mL; 45 mmol) was heated at 40° C. for 10 min, then the temperature was increased to 60° C. and after 20 min the mixture was heated at reflux for 30 min. The solution was evaporated (40° C.; 2 kPa) and the residue was dissolved in CH₂Cl₂ (5×4 mL) evaporating the solvent each time. The final residue was dissolved in CH₂Cl₂ (50 mL) and dropped into a solution of N²,N²-bis[2-[bis[2-(1,1-dimethylethoxy)-2-oxoethyl]amino]ethyl]-L-lysine 1,1-dimethylethyl ester, prepared according to Example 2, (11 g; 14.7 mmol) in CHCl₃ (150 mL), maintaining the mixture at 5÷10° C. The resulting solution was washed with a saturated aqueous solution of NaHCO₃ (3×50 mL); the organic phase was dried over Na₂SO₄ and concentrated to dryness to yield an oil (20 g) which was purified by flash chromatography:

Column: 60 mm; h=350 mm; Stationary phase: Silica gel 230–400 mesh Merck KGaA art 9385 (0.5 kg); Mobile phase: 7/3 n-hexane/EtOAc. The desired product was obtained (11.3 g; 11.9 mmol). Yield 79%. Acidic titer (0.1 N HClO₄): 95%; TLC: Rf 0.39; Stationary phase: Silica gel plates 60 F$_{254}$ Merck KGaA art 5715; Mobile phase: 8/2 n-hexane/EtOAc; Detection: 1% KMnO₄ in 1 M NaOH; ¹³C-NMR, ¹H-NMR and MS spectra were consistent with the structure. Weight loss: (80° C.) 3.81%; Elemental analysis (%):

|  | C | H | N |
|---|---|---|---|
| Calcd. | 65.65 | 9.96 | 5.89 |
| Found | 65.73 | 10.09 | 5.78 |

B) N',N'-bis[2-[bis(Carboxymethyl)amino]ethyl]-N'-(dicyclohexylacetyl)-L-lysine

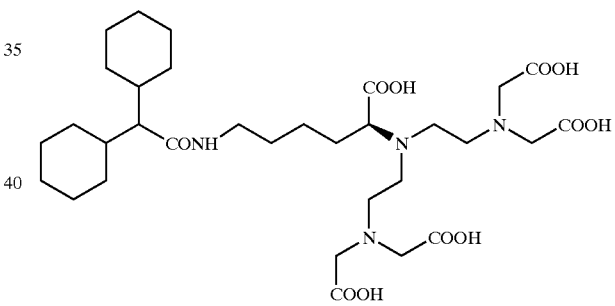

A solution of the pentaester from the previous preparation (9 g; 9.4 mmol) in CF₃COOH (110 mL; 1.44 mol) was stirred over 40 h under N₂ atmosphere. After evaporation (40° C.; 2 kPa) the residue was dissolved in CH₂Cl₂ (5×100 mL) evaporating the solvent each time (40° C.; 2 kPa). The crude was dissolved in a 9/1 H₂O/CH₃CN mixture and the solution was loaded onto a column of Amberlite® XAD 16-00 polystyrene resin (300 mL). The column was eluted at first with H₂O (1.5 L) then elution with 4/1 H₂O/CH₃CN (1.5 L) afforded the product. After concentration to 300 mL the resulting solution was filtered over Millipore HA 0.45 m and concentrated to the final volume of 100 mL. After 1 h at 20° C. the precipitate was filtered and dried (40° C.; 2 kPa; P₂O₅) to yield the desired product (3.05 g; 4.5 mmol). Yield 48%.

mp: 145° C. (dec.); Acidic titer (0.1 N NaOH): 95%; Complexometric titer (0.001 N GdCl₃): 96.3%; HPLC: 99.2% (area %)—Chromatographic method: Stationary phase: Lichrosorb RP-Select B 5 mm; 250×4 mm column packed by Merck KGaA; Temperature: 45° C.; Mobile phase: gradient elution; A=0.017 M H₃PO₄ in water; B=CH₃CN;

| Gradient timetable: | min | % A | % B |
|---|---|---|---|
| | 0 | 95 | 5 |
| | 5 | 95 | 5 |
| | 30 | 20 | 80 |
| | 45 | 20 | 80 |

Flow rate: 1 mL min$^{-1}$; Detection (UV): 210 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector. K.F.: 2.09%; $^{13}$C-NMR, $^1$H-NMR, MS and IR spectra were consistent with the structure.
Elemental analysis (%):

| | C | H | N | F | |
|---|---|---|---|---|---|
| Calcd. | 57.30 | 8.11 | 8.35 | — | |
| Found | 57.58 | 8.20 | 8.35 | <0.1 | anhydrous |

$[\alpha]^{20}$(c 2.5; 0.1 M NaOH);

| λ (nm) | 589 | 578 | 546 | 436 | 405 | 365 |
|---|---|---|---|---|---|---|
| $[\alpha]^{20}{}_\lambda$ | −9.80° | −11.48° | −13.44° | −20.72° | −24.12° | −29.80° |

C) [[N$^2$,N$^2$-bis[2-[bis(Carboxymethyl)amino]ethyl]-N$^6$-(dicyclohexylacetyl)-L-lysinate(5-)]gadolinate(2-)] dihydrogen Compound with 1-Deoxy-1-methylamino-D-glucitol (1:2)

A 1 M aqueous solution of 1-deoxy-1-methylamino-D-glucitol (9.5 mL; 9.5 mmol) was dropped into a stirred suspension of the free ligand from the previous preparation (2.23 g; 3.3 mmol) in H$_2$O (50 mL) to give a clear solution. A 0.1 M solution of GdCl$_3$ (32.5 mL; 3.25 mmol) was slowly added, maintaining the pH of the mixture at 5.5 by addition of a 1 M aqueous solution of 1-deoxy-1-methylamino-D-glucitol. After stirring for 1 h at room temperature the solution was filtered over Millipore® HA 0.45 m and loaded onto a column of Amberlite® XAD 16-00 polystyrene resin (200 mL). The column was eluted with water (300 mL) followed by 3/1 H$_2$O/CH$_3$CN mixture. The fractions containing the complex were combined and, after concentration to 150 mL, the resulting cloudy solution was filtered over Millipore® HA 0.45 m. The solution was evaporated to 20 mL and the pH was corrected from 8.5 to 7 with 0.1 M HCl (0.6 mL). The resulting solution was evaporated to dryness to give the title compound (3.6 g; 3 mmol). Yield 91%.

mp: 152° C. (dec.); Free ligand (0.001 M GdCl$_3$):<0.1%; HPLC: 99.5% (area %)—Chromatographic method: Stationary phase: Lichrospher 100 RP-8 5 μm; 250×4 mm column packed by Merck KGaA; Temperature: 40° C.; Mobile phase: isocratic elution with premixed mobile phase: 1 g of n-octylamine is added to 400 mL of acetonitrile mixed with 600 mL of water. The solution is buffered to pH 6 with H$_3$PO$_4$; Flow rate: 1 mL min$^{-1}$; Detection (UV): 210 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector. K.F.: 2.46%; MS and IR spectra were consistent with the structure. Elemental analysis (%):

| | C | H | Gd | N |
|---|---|---|---|---|
| Calcd. | 45.46 | 7.05 | 12.94 | 6.91 |
| Found | 45.32 | 7.16 | 12.60 | 6.81 |

EXAMPLE 10

[[N,N-bis[2-[bis(Carboxymethyl)amino]ethyl]-L-tryptophanate(5-)]gadolinate(2-)]dihydrogen Compound with 1-Deoxy-1-(methylamino)-D-glucitol (1:2)

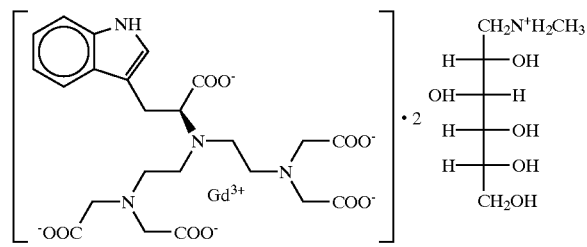

A) L-Tryptophan Methyl Ester Hydrochloride

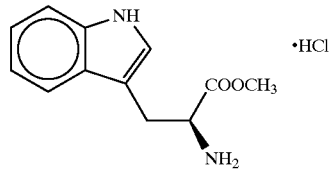

A 1.2 M solution of HCl in MeOH (440 mL; 0.528 mol) was added to a suspension of L-tryptophan (commercial product) (30.6 g; 150 mmol) in MeOH (70 mL). The resulting clear solution was stirred for 5 days at 20° C. The solution was concentrated (35° C.; 1.3 kPa) to yield a solid which was dissolved in MeOH (10 mL). Et$_2$O (300 mL) was added to the solution and the mixture was vigorously stirred for 1 h. The mixture was filtered and the solid was washed with Et$_2$O (70 mL). The combined solutions were concentrated (35° C.; 1.3 kPa) to a volume of 100 mL and filtered. The solid materials were combined and dried (40° C.; P2O5; 1.3 kPa) to give as a white solid the desired product (38.5 g; 149.5 mmol). Quantitative yield.

mp: 211° C. dec. Argentometric titer (0.1 M AgNO$_3$): 102%; HPLC : 99.7% (area %) Chromatographic method: the same of Ex. 4, Step A); TLC: Rf 0.38; Stationary phase: Silica gel plates 60 F$_{254}$ Merck KGaA art 5715; Mobile phase: 9:1 CH$_2$Cl$_2$:MeOH; Detection: 1% KMnO$_4$ in 1 M NaOH; $^{13}$C-NMR, $^1$H-NMR, MS and IR spectra were consistent with the structure. $[\alpha]^{20}$(c 2.2; CH$_3$OH):

| λ(nm) | 589 | 578 | 546 | 436 | 405 |
|---|---|---|---|---|---|
| $[\alpha]^{20}{}_\lambda$ | +17.9° | +18.91° | +22.01° | +45.03° | +59.27° |

Elemental analysis (%):

|       | C     | H    | N     | Cl    |
|-------|-------|------|-------|-------|
| Calcd. | 56.68 | 5.94 | 11.00 | 13.92 |
| Found  | 56.71 | 5.97 | 11.08 | 13.75 |

B) N,N-bis[2-[bis[2-(1,1-Dimethylethoxy)-2-oxo-ethyl]amino]ethyl]-L-tryptophan Methyl Ester

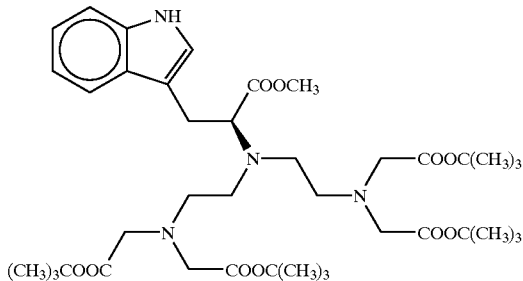

A suspension of L-Tryptophan methyl ester hydrochloride (12.9 g; 50 mmol) in $CH_2Cl_2$ (150 mL) was washed with a saturated aq. solution of $NaHCO_3$ until basic pH of the aqueous phase. After separation the organic phase was dried ($Na_2SO_4$) and concentrated (35° C.; 1.3 kPa) to yield an oil, that was dissolved in $CH_3CN$ (500 ML). N-(2-bromoethyl)-N-[2-(1,1-dimethylethoxy)-2-oxoethyl]glycine 1,1-dimethylethyl ester, prepared according to Example 1, (17.6 g; 50 mmol) and 2 M pH 7 phosphate buffer (500 mL) were then added. The mixture was vigorously stirred for 3 h, then N-(2-bromoethyl)-N-[2-(1,1-dimethylethoxy)-2-oxoethyl]glycine 1,1-dimethylethyl ester (16.7 g; 47 mmol) was added and the mixture was stirred for 16 h. After further addition of N-(2-bromoethyl)-N-[2-(1,1-dimethylethoxy)-2-oxo-ethyl]glycine 1,1-dimethylethyl ester (3.5 g; 10 mmol) and stirring for 3 h the reaction was stopped. The phases were separated and the organic phase was evaporated to dryness (35° C.; 1.3 kPa). The residue was suspended in $Et_2O$ (500 mL) and washed with brine (2×100 mL) and with $H_2O$ (50 mL). The organic phase was dried ($Na_2SO_4$) and evaporated to yield an oil (39.8 g), which was purified by flash chromatography:

Silica gel column; Stationary phase: Silica gel 230–400 mesh Merck KGaA art 9385 (1 kg); Mobile phase: 7:3 n-hexane: EtOAc (10 L)). The desired product was obtained (6.22 g; 34.4 mmol). Yield 69%; mp: 71° C.; Acidic titer (0.1 M $HClO_4$): 97.4%; TLC: Rf 0.44; Stationary phase: Silica gel plates 60 $F_{254}$ Merck KGaA art 5715; Mobile phase: 6:4 n-hexane:EtOAc; Detection: 1% $KMnO_4$ in 1 M NaOH; HPLC: 99.3% (area %) Chromatographic method: the same of Ex. 4, Step A); $^{13}$C-NMR, $^1$H-NMR, MS and IR spectra were consistent with the structure. $[\alpha]^{20}$(c 2.2; $CHCl_3$):

| λ(nm) | 589 | 578 | 546 | 436 | 405 |
|-------|-----|-----|-----|-----|-----|
| $[\alpha]^{20}{}_\lambda$ | −17.86° | −18.50° | −21.12° | −38.35° | −47.78° |

Elemental analysis (%):

|       | C     | H    | N     |
|-------|-------|------|-------|
| Calcd. | 63.13 | 8.48 | 7.36 |
| Found  | 63.11 | 8.59 | 7.10 |

C) N,N-bis[2-[bis(Carboxymethyl)amino]ethyl]-L-tryptophan

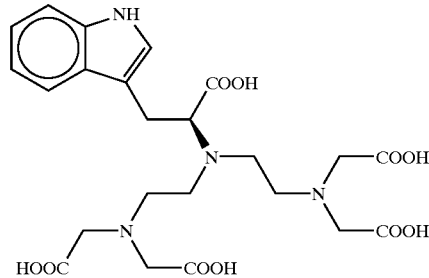

A 0.5 M solution of $H_2SO_4$ (162 mL; 81 mmol) was added to a suspension of the pentaester from the previous preparation (24 g; 31.5 mmol) in $H_2O$ (160 mL) over 15 min. The mixture was stirred at 90° C. for 2.5 h. The resulting clear solution was cooled and the pH was adjusted to 13.5 by adding 6 M NaOH. The mixture was stirred at 20° C. for 16 h. The pH was adjusted to 1.5 by adding 2 M HCl and the solution loaded onto a column of Amberlite® XAD 1600 polystyrene resin (1 L). Elution with 9:1 $H_2O/CH_3CN$ afforded the free ligand (13.3 g; 25.4 mmol). Yield 80%.

mp: 142° C. (dec.); Acidic titer (0.1 M NaOH): 103.2%; Acidic titer (0.1 M $HClO_4$): 102.9%; Complexometric titer (0.1 M $ZnSO_4$): 103%; Complexometric titer (0.001 M $GdCl_3$): 103%; HPLC: 98.8% (area %) Chromatographic method: the same of Ex. 4, Step A); TLC: Rf 0.08; Stationary phase: Silica gel plates 60 $F_{254}$ Merck KGaA art 5715; Mobile phase: 6:3:1 $CHCl_3$:MeOH:25% aq. $NH_4OH$; Detection: 1% $KMnO_4$ in 1 M NaOH; K.F.: 4.16%; $^{13}$C-NMR, $^1$H-NMR, MS and IR spectra were consistent with the structure. $[\alpha]^{20}$(c 2.6; 0.02 N NaOH):

| λ(nm) | 589 | 578 | 546 | 436 |
|-------|-----|-----|-----|-----|
| $[\alpha]^{20}{}_\lambda$ | −13.34° | −14.07° | −16.18° | −26.92° |

Elemental analysis (%):

|       | C     | H    | N     |           |
|-------|-------|------|-------|-----------|
| Calcd. | 52.87 | 5.79 | 10.72 |           |
| Found  | 53.09 | 5.94 | 10.71 | anhydrous |

D) [[N,N-bis[2-[bis(Carboxymethyl)amino]ethyl]-L-tryptophanate-(5-)]gadolinate(2-)]dihydrogen Compound with 1-Deoxy-1-(methylamino)-D-glucitol (1:2)

A mixture of the free ligand from the previous preparation (9.4 g; 17.5 mmol), $Gd_2O_3$ (3.17 g; 8.77 mmol) and 1.01 M 1-deoxy-1-(methylamino)-D-glucitol (31.62 mL; 32 mmol) in $H_2O$ (970 mL) was stirred for 16 h at 50° C. The mixture was filtered over Millipore® (HAWP 0.45 m) and loaded onto a column of Amberlite® XAD-1600 polystyrene resin (1 L). The product was obtained by elution with 95:5 $H_2O$:$CH_3CN$. The eluate was concentrated to 1 L and, after adjusting the pH to 7 with a 1 M 1-deoxy-1-(methylamino)-

D-glucitol solution, was evaporated to dryness (1.3 kPa; 40° C.; $P_2O_5$) to yield the title compound (18.1 g; 17 mmol). Yield 97%.

mp: 148° C. (dec.); Free ligand (0.001 M $GdCl_3$): <0.1%; HPLC: 98.6% (area %) Chromatographic method: Stationary phase: Lichrospher 100 RP-8 5 μm; 250×4 mm column packed by Merck KGaA; Temperature: 40° C.;

Mobile phase: isocratic elution with premixed mobile phase: 1 g of n-octylamine is added to 270 mL of acetonitrile mixed with 730 mL of water. The solution is buffered to pH 6 with $H_3PO_4$;

Flow rate: 1 mL min$^{-1}$; Detection (UV): 210 nm; Injection: 5 μL; Sample concentration: 1 mg mL$^{-1}$; Instrumentation: Merck KGaA high pressure gradient pump system (L6200 and L6000), Merck KGaA—Hitachi AS 2000 autosampler, Merck KGaA T 6300 column thermostat, Merck KGaA—Hitachi L 4500 diode array detector, Merck KGaA. K.F.: 3.66%; MS spectrum was consistent with the structure. Elemental analysis (%):

| | C | H | Gd | N | O | |
|---|---|---|---|---|---|---|
| Calcd. | 41.64 | 5.76 | 14.74 | 7.87 | 29.98 | |
| Found | 41.98 | 5.90 | 14.63 | 7.82 | 29.30 | anhydrous |

EXAMPLE 11

[[N,N-bis[2-[bis(Carboxymethyl)amino]ethyl]-O-(4-hydroxyphenyl)-3,5-diiodo-D-tyrosinato(5-)]gadolinate(2-)]dihydrogen Compound with 1-Deoxy-1-(methylamino)-D-glucitol (1:2)

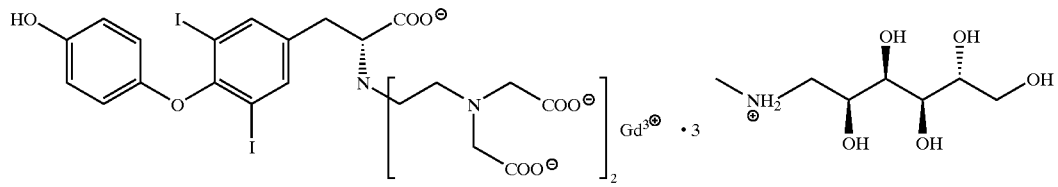

A) N,N-bis[2-[bis(Carboxymethyl)amino]ethyl]-O-(4-hydroxyphenyl)-3,5-diiodo-D-tyrosine

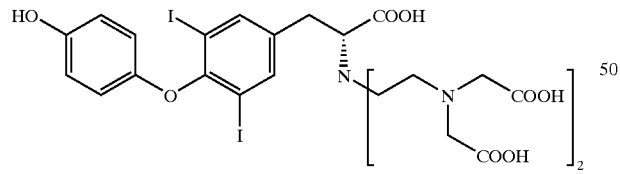

The compound was prepared according to Example 4 Step C, starting from O-(4-hydroxyphenyl)-3,5-diiodo-D-tyrosine. Yield 52%.

mp: 170–175° C. (dec.); Complexometric titer (0.001 M $GdCl_3$): 99%; HPLC: 100% (area %) Chromatographic method: Stationary phase: Lichrosorb RP-Select B 5 μm; 250×4 mm column packed by Merck KGaA; Temperature: 45° C.; Mobile phase: gradient elution; A=0.017 M $H_3PO_4$ in water; B=$CH_3CN$;

| Gradient timetable: | min | % A | % B |
|---|---|---|---|
| | 0 | 95 | 5 |
| | 5 | 95 | 5 |
| | 30 | 20 | 80 |
| | 45 | 20 | 80 |

Flow rate: 1 mL min$^{-1}$; Detection (UV): 210 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector. $^{13}$C-NMR, $^1$H-NMR, MS and IR spectra were consistent with the structure. $[\alpha]_D^{20}$ (c 2.5; 1 M NaOH):−6.1.

B) [[N,N-bis[2-[bis(Carboxymethyl)amino]ethyl]-O-(4-hydroxyphenyl)-3,5-diiodo-D-tyrosinato(5-)]gadolinate (2-)]dihydrogen Compound with 1-Deoxy-1-(methylamino)-D-glucitol (1:2)

The ligand from the previous preparation was dissolved in $H_2O$ and 1 M aq. meglumine at pH 6.5, then complexed at pH 6.8 with 1 M aq.$GdCl_3$ and nanofiltered. Yield 86%.

mp: 180–186° C.; Free ligand (0.001 M $GdCl_3$): <0.1%; HPLC: 100% (area %) Chromatographic method: Stationary phase: Lichrospher 100 RP-8 5 μm; 250×4 mm column packed by Merck KGaA; Temperature: 40° C.; Mobile phase: isocratic elution with premixed mobile phase is obtained by addition of n-octylamine (1 g) and 0.1 M EDTA disodium salt (10 mL) to a mixture of $CH_3CN$ (300 mL) and $H_2O$ (690 mL) buffering to pH 6 with $H_3PO_4$; Flow rate: 1 mL min$^{-1}$; Detection (UV): 245 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector. K.F.: 2.90%; MS and IR spectra were consistent with the structure. Elemental analysis (%):

| | C | H | Gd | I | N | |
|---|---|---|---|---|---|---|
| Calcd. | 35.48 | 4.50 | 11.33 | 18.29 | 5.05 | |
| Found | 35.36 | 4.46 | 11.34 | 18.29 | 5.06 | Anhydrous |

EXAMPLE 12

[[N,N-bis[2-[bis(Carboxymethyl)amino]ethyl]-O-(4-hydroxy-3-iodophenyl)-L-tyrosinato(5-)]gadolinate(2-)]dihydrogen Compound with 1-Deoxy-1-(methylamino)-D-glucitol (1:2)

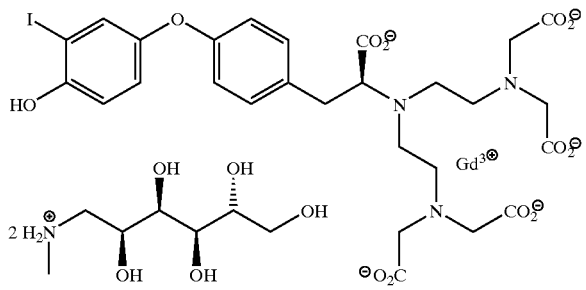

A) [[N,N-bis[2-[bis(Carboxymethyl)amino]ethyl]-O-(4-hydroxy-3-iodophenyl)-L-tyrosine

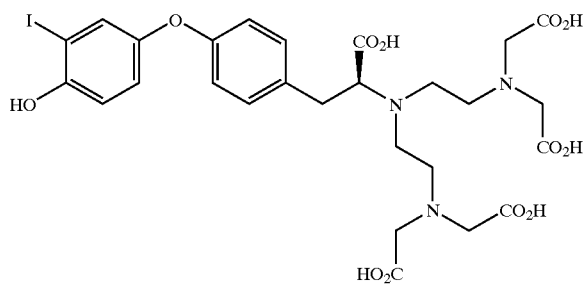

N,N-bis[2-[bis[2-(1,1-dimethylethoxy)-2-oxoethyl]amino]ethyl]-O-(4-hydroxyphenyl)-3,5-diiodo-L-tyrosine methyl ester, prepared according to Example 4 Step B, was deiodinated by catalytic hydrogenation with Pd on carbon, in MeOH/H$_2$O, at room temperature and atmospheric pressure, mantaining pH 7 by addition of 2 M NaOH. The deiodinated pentaester was deprotected at first with TFA in CH$_2$Cl$_2$, for 16 h at room temperature and then with NaOH in H$_2$O at pH 13. The ligand obtained by precipitation with HCl at pH $_{1.6}$ was monoiodinated in the outer ring with I$_2$/KI at room temperature. The solution was then acidified to pH 1.5 with 37% HCl and purified by preparative HPLC to afford the ligand. Yield 35%.

mp: 163–167° C.; Argentometric titer (0.1 M AgNO$_3$): 99.4%; HPLC: 99.8% (area %) Chromatographic method: Stationary phase: Lichrosorb RP-Select B 5 μm; 250×4 mm column packed by Merck KGaA; Temperature: 45° C.; Mobile phase: gradient elution; A=0.017 M H$_3$PO$_4$ in water; B=CH$_3$CN;

| Gradient timetable: | min | % A | % B |
|---|---|---|---|
| | 0 | 95 | 5 |
| | 30 | 20 | 80 |

Flow rate: 1 mL min$^{-1}$; Detection (UV): 210 nm; Injection: 10 μL; Sample concentration: 1 mg mL$^{-1}$; Instrumentation: Hewlett—Packard HP 1090 L liquid chromatograph equipped with DR 5 solvent delivery system, autosampler, column thermostat and diode array detector. K.F.: 2.20%; $^{13}$C-NMR, $^1$H-NMR, MS and IR spectra were consistent with the structure. $[\alpha]_{405}^{20}$ (c 1.02; 1 M NaOH): +16.34; Elemental analysis (%):

| | C | H | N | I | |
|---|---|---|---|---|---|
| Calcd. | 45.20 | 4.50 | 5.86 | 17.69 | |
| Found | 45.27 | 4.35 | 5.85 | 17.36 | anhydrous |

B) [[N,N-bis[2-[bis(Carboxymethyl)amino]ethyl]-O-(4-hydroxy-3-iodophenyl)-L-tyrosinato(5-)]gadolinate(2-)]dihydrogen Compound with 1-Deoxy-1-(methylamino)-D-glucitol (1:2).

The title complex was prepared in analogy to Example 11 Step B. Yield 92%.

mp: 164–167° C.; HPLC: 100% (area %) Chromatographic method: Stationary phase: Lichrospher 100 RP-8 5 μm; 250×4 mm column packed by Merck KGaA; Temperature: 40° C.; Mobile phase: isocratic elution with premixed mobile phase is obtained by addition of n-octylamine (1 g) and 0.5 mmol of EDTA to a mixture of CH$_3$CN (300 mL) and H$_2$O (700 mL) buffering to pH 6 with H$_3$PO$_4$; Flow rate: 1 mL min$^{-1}$; Detection (UV): 210 nm; Injection: 10 μL; Sample concentration: 1 mg mL$^{-1}$; Instrumentation: Merck KGaA—Hitachi high pressure gradient pump system (L6200 and L6000), Merck KGaA—Hitachi AS 2000 autosampler, Merck KGaA T 6300 column thermostat, Merck KGaA—Hitachi L 4500 diode array detector. K.F.: 1.44%; MS and IR spectra were consistent with the structure. Elemental analysis (%):

| | C | H | Gd | I | N | |
|---|---|---|---|---|---|---|
| Calcd. | 39.01 | 5.03 | 12.46 | 10.05 | 5.55 | |
| Found | 39.28 | 5.13 | 12.53 | 10.00 | 5.63 | anhydrous |

EXAMPLE 13

[[N,N-bis[2-[bis(Carboxymethyl)amino]ethyl]-3,5-dibromo-O-(4-hydroxyphenyl)-L-tyrosinato(5-)]gadolinate(2-)]dihydrogen Compound with 1-Deoxy-1-(methylamino)-D-glucitol (1:2)

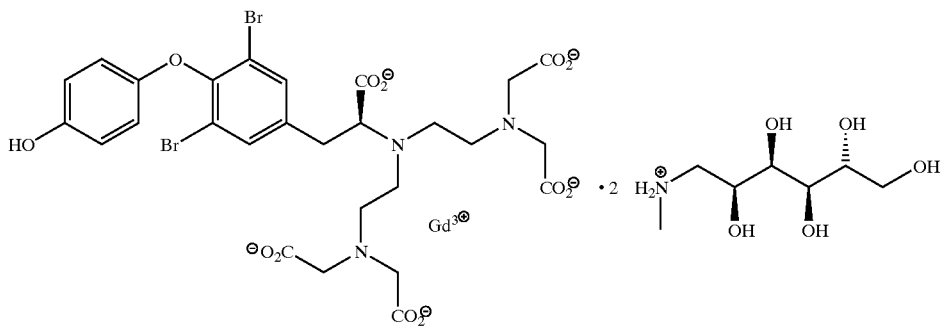

A) N,N-bis[2-[bis(Carboxymethyl)amino]ethyl]-3,5-dibromo-O-(4-hydroxyphenyl)-L-tyrosine

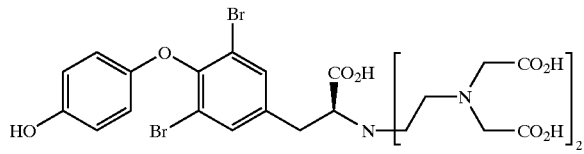

N-Acetyl-3,5-diamino-O-(4-methoxyphenyl)-L-tyrosine ethyl ester, (prepared according to: Chalmers J. R., Dickson G. T., Elks J. And Hems D. A., "The Synthesis of Thyroxine and Related Substances", Part V., J. Chem. Soc. (1949), 3424–3433), was diazotized with $NaNO_2$, AcOH and 98% $H_2SO_4$ at −10° C. and then brominated with a mixture of CuBr in 48% HBr and $CHCl_3$ at 10° C. for 2 h. After purification by column chromatography and deprotection with AcOH/57% $HI/H_2O$ at reflux for 48 h, 3,5-dibromo-O-(4-hydroxyphenyl)-L-tyrosine was transformed into the corresponding methyl ester by reaction with $SOCl_2$ in $CH_3OH/CH_2Cl_2$ for 48 h. The ester was then alkylated with N-(2-bromoethyl)-N-[2-(1,1-dimethylethoxy)-2-oxoethyl] glycine 1,1-dimethylethyl ester, (prepared according to Example 1), in $CH_3CN$ and 2 M pH 8 phosphate buffer for 48 h. The pentaester, after purification by flash chromatography, was deprotected with 0.25 M $H_2SO_4$ at reflux for 28 h, to give the precipitation of the ligand after cooling at room temperature. Yield 20%.

mp: 182–184° C.; Acidimetric titer: 99.4%; HPLC: 100% (area %) Chromatographic method: the same of Ex. 12, Step A; K.F.: 2.39%; $^{13}$C-NMR, $^1$H-NMR, MS and IR spectra were consistent with the structure.

| | Elemental analysis (%): | | | | |
| --- | --- | --- | --- | --- | --- |
| | C | H | Br | N | |
| Calcd. | 43.27 | 4.17 | 21.32 | 5.61 | |
| Found | 43.13 | 4.20 | 21.61 | 5.53 | anhydrous |

B) [[N,N-bis[2-[bis(Carboxymethyl)amino]ethyl]-3,5-dibromo-O-(4-hydroxyphenyl)-L-tyrosinato(5-)]gadolinate(2-)]dihydrogen Compound with 1-Deoxy-1-(methylamino)-D-glucitol (1:2)

The title complex was prepared in analogy to Example 12 Step B. Yield 95%.; mp: 185–190° C.; HPLC: 99.1% (area %) Chromatographic method: the same of Ex. 12, Step B; K.F.: 2.64%; MS and IR spectra were consistent with the structure.

| | Elemental analysis (%): | | | | | |
| --- | --- | --- | --- | --- | --- | --- |
| | C | H | Gd | Br | N | |
| Calcd. | 38.06 | 4.83 | 12.15 | 12.35 | 5.41 | |
| Found | 38.27 | 5.03 | 12.25 | 12.07 | 5.41 | anhydrous |

EXAMPLE 14

[[N,N-bis[2-[bis(Carboxymethyl)amino]ethyl]-3,5-dibromo-O-(4-hydroxy-3-iodophenyl)-L-tyrosinato(5-)]gadolinate(2-)]dihydrogen Compound with 1-Deoxy-1-(methylamino)-D-glucitol (1:2)

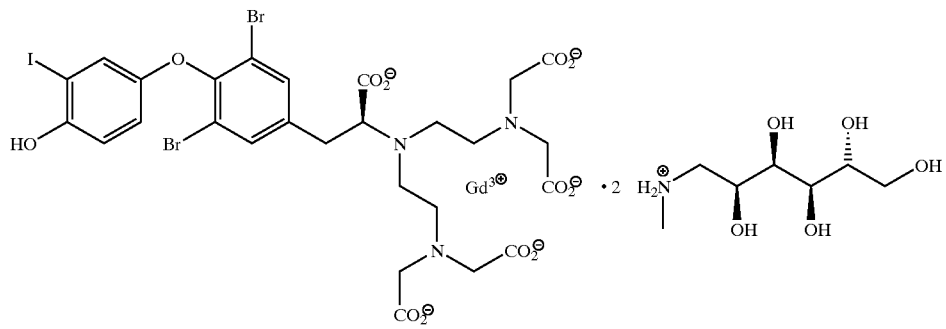

A) N,N-bis[2-[bis(Carboxymethyl)amino]ethyl]-3,5-dibromo-O-(3-iodophenyl)-L-tyrosine

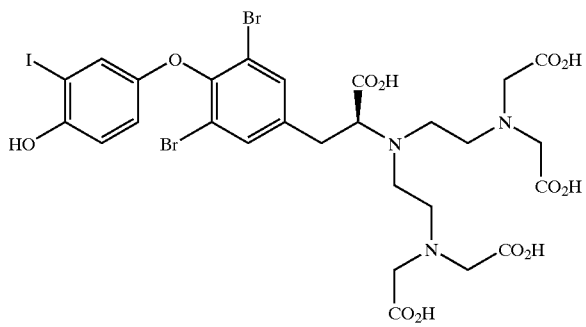

N,N-Bis[2-[bis(carboxymethyl)amino]ethyl]-3,5-dibromo-O-(4-hydroxyphenyl)-L-tyrosine, prepared according to Example 13 Step A, was monoiodinated in the outer ring with $I_2$/KI at room temperature. The solution was concentrated, then acidified to pH 1 with 37% HCl and purified by preparative HPLC. Yield 61%.

mp: 191° C.; HPLC: 99.5% (area %) Chromatographic method: the same of Ex. 11, Step A; K.F.: 2.22%; $^{13}$C-NMR, $^1$H-NMR, MS and IR spectra were consistent with the structure.

| | Elemental analysis (%): | | | | | |
|---|---|---|---|---|---|---|
| | C | H | Br | I | N | |
| Calcd. | 37.05 | 3.45 | 18.26 | 14.50 | 4.80 | |
| Found | 37.53 | 3.27 | 17.67 | 14.34 | 4.71 | anhydrous |

B) [[N,N-bis[2-[bis(Carboxymethyl)amino]ethyl]-3,5-dibromo-O-(4-hydroxy-3-iodophenyl)-L-tyrosinato(5-)]gadolinate(2-)]dihydrogen Compound with 1-Deoxy-1-(methylamino)-D-glucitol (1:2)

The ligand from the previous preparation was complexed with $GdCl_3$ following the procedure reported in Example 11 Step B. Yield 92%.

mp: 180–185° C.; Free ligand (0.001 M $GdCl_3$): 0.10%; HPLC: 98.3% (area %) Chromatographic method: Stationary phase: Inertsil ODS-3 5 μm; 250×4 mm column packed by GL Sciences; Temperature: 40° C.; Mobile phase: gradient elution; A=0.005 M $KH_2PO_4$, 0.005 M $K_2HPO_4$, 0.3 mM; EDTA in water; B=$CH_3CN$;

| Gradient timetable: | min | % A | % B |
|---|---|---|---|
| | 0 | 80 | 20 |
| | 15 | 60 | 40 |
| | 25 | 60 | 40 |

Flow rate: 1 mL min$^{-1}$; Detection (UV): 210 nm; Injection: 10 μL; Sample concentration: 1 mg mL$^{-1}$; Instrumentation: Hewlett—Packard HP 1090 M liquid chromatograph equipped with DR 5 solvent delivery system, autosampler, column thermostat and diode array detector. Weight loss (100° C.): 1.01%; MS and IR spectra were consistent with the structure.

Elemental analysis (%):

| | C | H | Gd | Br | I | N |
|---|---|---|---|---|---|---|
| Calcd. | 34.68 | 4.33 | 11.07 | 11.25 | 8.94 | 4.93 |
| Found | 34.68 | 4.41 | 11.07 | 11.03 | 9.04 | 5.00 |

EXAMPLE 15

[[N,N-bis[2-[bis(Carboxymethyl)amino]ethyl]-3,5-dibromo-O-(4-hydroxy-3-iodophenyl)-L-tyrosinato(5-)]gadolinate(2-)]dihydrogen Compound with 1-Deoxy-1-(methylamino)-D-glucitol (1:3)

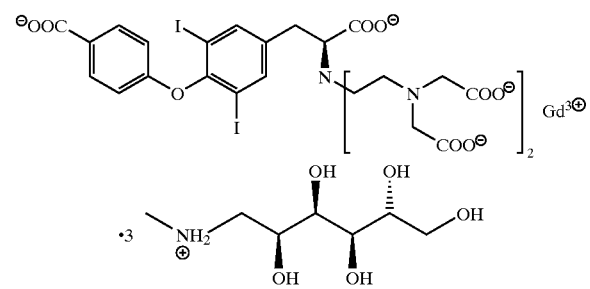

A) N,N-bis[2-[bis(Carboxymethyl)amino]ethyl]-O-(4-carboxyphenyl)-3,5-diiodo-L-tyrosine

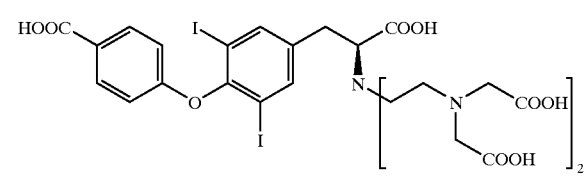

Reaction of N-acetyl-3,5-dinitro-L-tyrosine ethyl ester, (prepared according to: Chalmers J. R., Dickson G. T., Elks J. And Hems D. A., "The Synthesis of Thyroxine and Related Substances", Part V., J. Chem. Soc. (1949), 3424–3433), with methyl 4-hydroxybenzoate and toluene-4-sulfonyl chloride in pyridine at 120° C. for 2.5 h, followed by catalytic hydrogenation with Pd on carbon at 40° C. and atmospheric pressure in $CH_3OH$ afforded the diamino derivative, which was isolated as the disulfate. Thus compound was diazotized ($AcOH/H_2SO_4$; $NaNO_2$), then diiodinated with $I_2$/KI and finally deprotected in HCl/AcOH at 100° C. for 2.5 h to give O-(4-carboxyphenyl)-3,5-diiodo-L-tyrosine. The aminoacid was esterified with $SOCl_2$ in $CH_2Cl_2/CH_3OH$ at room temperature for 42 h and then alkylated with N-(2-bromoethyl)-N-[2-(1,1-dimethylethoxy)-2-oxoethyl]glycine 1,1-dimethylethyl ester, (prepared according to Example 1), in $CH_3CN$ and 2 M pH 8 phosphate buffer for 166 h. After separation, the organic phase was evaporated and the residue purified by flash chromatography. The hexaester thus obtained was deprotected at first with TFA at room temperature for 16 h, then with 1.5 M NaOH for 16 h and the ligand precipitated with aq. HCl at pH 1.5. Yield 24%.

mp: 185–190° C. (dec.); Complexometric titer (0.1 M $ZnSO_4$): 97%; HPLC: 100% (area %) Chromatographic method: Stationary phase: Lichrospher 100 RP-8 5 μm; 250×4 mm column packed by Merck KGaA; Temperature: 45° C.; Mobile phase: gradient elution; A=0.01 M $KH_2PO_4$, 1 mM EDTA in water; B=$CH_3CN$;

| Gradient timetable: | min | % A | % B |
|---|---|---|---|
| | 0 | 95 | 5 |
| | 30 | 20 | 80 |
| | 45 | 20 | 80 |

Flow rate: 1 mL min$^{-1}$; Detection (UV): 210 nm; Injection: 10 µL; Sample concentration: 1 mg mL$^{-1}$; Instrumentation: Hewlett—Packard HP 1090 L liquid chromatograph equipped with DR 5 solvent delivery system, autosampler, column thermostat and diode array detector. K.F.: 1.02%; $^{13}$C-NMR, $^1$H-NMR, MS and IR spectra were consistent with the structure. $[\alpha]_D^{20}$ (c 2.01; 1 M NaOH): +7.21;

| | Elemental analysis (%): | | | | |
|---|---|---|---|---|---|
| | C | H | I | N | |
| Calcd. | 38.60 | 3.59 | 29.13 | 4.82 | |
| Found | 38.41 | 3.66 | 28.84 | 4.74 | anhydrous |

B) [[N,N-bis[2-[bis(Carboxymethyl)amino]ethyl]-O-(4-carboxyphenyl)-3,5-diiodo-L-tyrosinato(6-)]gadolinate(3-)] trihydrogen Compound with 1-Deoxy-1-(methylamino)-D-glucitol (1:3)

The compound was prepared according to Example 11 Step B. Yield 95%. mp: 150–156° C.; HPLC: 100% (area %) Chromatographic method: Stationary phase: Inertsil ODS-2 5 µm; 250×4 mm column packed by GL Sciences; Temperature: 40° C.; Mobile phase: isocratic elution with premixed mobile phase is obtained by addition of n-octylamine (1 g) and 0.3 mmol of EDTA to a mixture of CH$_3$CN (370 mL) and H$_2$O (630 mL) buffering to pH 6 with H$_3$PO$_4$; Flow rate: 1 mL min$^{-1}$; Detection (UV): 210 nm; Injection: 10 µL; Sample concentration: 1 mg mL$^{-1}$; Instrumentation: Hewlett—Packard HP 1090 M liquid chromatograph equipped with DR 5 solvent delivery system, autosampler, column thermostat and diode array detector. Weight loss (80° C.): 2.19%; MS and IR spectra were consistent with the structure.

| | Elemental analysis (%) | | | | |
|---|---|---|---|---|---|
| | C | H | Gd | I | N |
| Calcd. | 36.53 | 4.94 | 9.76 | 15.75 | 5.22 |
| Found | 35.88 | 5.08 | 9.68 | 15.43 | 5.14 |

EXAMPLE 16

[[N,N-bis[2-[bis(Carboxymethyl)amino]ethyl]-O-(4-carboxyphenyl)-L-tyrosinato(6-)]gadolinate(3-)] trihydrogen Compound with 1-Deoxy-1-(methylamino)-D-glucitol (1:3)

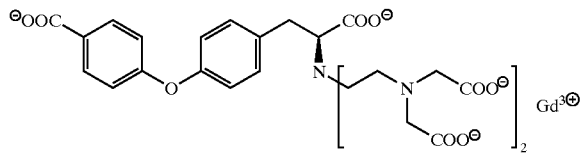

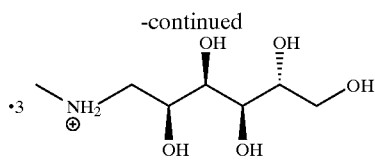

A) N,N-bis[2-[bis(Carboxymethyl)amino]ethyl]-O-(4-carboxyphenyl)-L-tyrosine

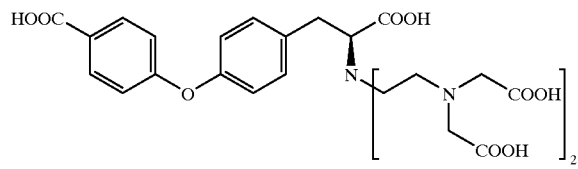

A solution of N,N-bis[2-[bis(Carboxymethyl)amino]ethyl]-O-(4-carboxyphenyl)-3,5-diiodo-L-tyrosine, prepared according to Example 15 Step A, in H$_2$O at pH 8, was deiodinated by catalytic hydrogenation with Pd on carbon, at room temperature and atmospheric pressure, maintaining pH 7.5–8.5 by addition of 2 M NaOH. The ligand was recovered after precipitation with aq. HCl. Yield 81%.

mp: 170–172° C. (dec.); Acidimetric titer (0.1 M NaOH): 98%; HPLC: 100% (area %) Chromatographic method: the same of Ex. 15, Step A; K.F.: 2.50%; $^{13}$C-NMR, $^1$H-NMR, MS and IR spectra were consistent with the structure. $[\alpha]_D^{20}$ (c 2.01; 1 M NaOH): +6.96;

| | Elemental analysis (%): | | | |
|---|---|---|---|---|
| | C | H | N | |
| Calcd. | 54.28 | 5.37 | 6.78 | |
| Found | 54.17 | 5.35 | 6.86 | anhydrous |

B) [[N,N-bis[2-[bis(Carboxymethyl)amino]ethyl]-O-(4-carboxyphenyl)-L-tyrosinato(6-)]gadolinate(3-)] trihydrogen Compound with 1-Deoxy-1-(methylamino)-D-glucitol (1:3)

The ligand from the previous preparation was complexed with GdCl$_3$ following the procedure reported in Example 11 Step B. Yield 83%.

mp: 110–114° C.; HPLC: 99.5% (area %) Chromatographic method: the same of Ex. 11, Step A; Weight loss: 3.06%; MS and IR spectra were consistent with the structure.

| | Elemental analysis (%): | | | |
|---|---|---|---|---|
| | C | H | Gd | N |
| Calcd. | 43.29 | 6.01 | 11.57 | 6.18 |
| Found | 42.57 | 6.11 | 11.27 | 6.06 |

EXAMPLE 17

[[(S)-N-[4-[bis[2-[bis(Carboxymethyl)amino]ethyl] amino]-4-carboxy-1-oxobutyl]-O-(4-hydroxyphenyl)-3,5-diiodo-L-tyrosinato(6-)]gadolinate(3-)]trisodium Salt

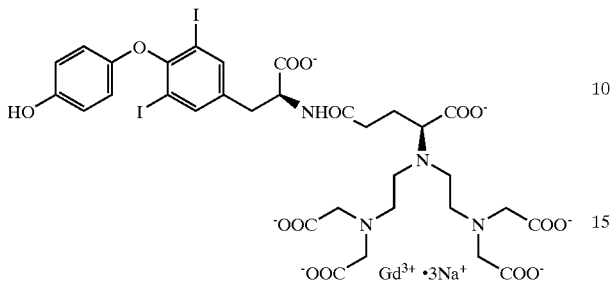

A) (S)-N-[4-[bis[2-[bis(Carboxymethyl)amino]ethyl] amino]-4-carboxy-1-oxobutyl]-O-(4-hydroxyphenyl)-3,5-diiodo-L-tyrosine

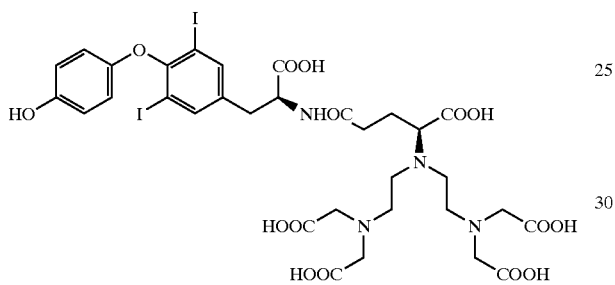

O-(4-Hydroxyphenyl)-3,5-diiodo-L-tyrosine methyl ester, prepared according to Example 4 Step A, was reacted with N,N-bis[2-[bis[2-(1,1-dimethylethoxy)-2-oxoethyl]amino]ethyl]-L-glutamic acid 1-(1,1-dimethyl-ethyl) ester (prepared according to: Anelli P. L., Fedeli F., Gazzotti O., Lattuada L., Lux G. and Rebasti F., "L-Glutamic Acid and L-Lysine as Useful Building Blocks for the Preparation of Bifuctional DTPA-like Ligand", Bioconjugate Chem. (1999), 10, 137–140), diethylphosphoryl cyanide (DEPC) and ethyldiisopropylamine (DIEA), in DMF, under nitrogen atmosphere at 0° C. After purification by flash chromatography, the pentaester was deprotected at first with TFA in $CH_2Cl_2$ at room temperature for 47 h, then with 2 M LiOH for 21 h. The solution was acidified to pH 3.3 with aq. HCl and loaded onto an Amberlite® XAD 1600 resin column. Eluting with a $H_2O/CH_3CN$ gradient afforded the ligand.

Yield 22%. mp: 211° C. (dec.); HPLC: 100% (area %) Chromatographic method: the same of Ex. 15, Step A; $^{13}$C-NMR, $^1$H-NMR, MS and IR spectra were consistent with the structure.

B) [[(S)-N-[4-[bis[2-[bis(Carboxymethyl)amino]ethyl] amino]-4-carboxy-1-oxobutyl]-O-(4-hydroxyphenyl)-3,5-diiodo-L-tyrosinato(6-)]gadolinate(3-)]trisodium Salt The ligand from the previous preparation was complexed with $Gd_2O_3$ at pH 6.5 and 40° C. for 18 h. After filtration, the solution was purified by three subsequent columns (Amberlite® XAD 1600 resin, Dowex® CCR3LB and again Amberlite® XAD 1600 resin). Yield 46%.

mp: >250° C.; Free ligand (0.001 M $GdCl_3$): <0.1%; HPLC: 100% (area %) Chromatographic method: Stationary phase: Inertsil ODS-3 5 µm; 250×4 mm column packed by GL Sciences; Temperature: 40° C.; Mobile phase: gradient elution; A=0.005 M $KH_2PO_4$ and 0.005 M $K_2HPO_4$ in water; B=$CH_3CN$;

| Gradient timetable: | min | % A | % B |
|---|---|---|---|
| | 0 | 79 | 21 |
| | 5 | 79 | 21 |
| | 10 | 60 | 40 |
| | 25 | 60 | 40 |

Flow rate: 1 mL min$^{-1}$; Detection (UV): 210 nm; Injection: 25 µL; Sample concentration: 3 mg mL$^{-1}$; Instrumentation: Hewlett—Packard HP 1090 M liquid chromatograph equipped with DR 5 solvent delivery system, autosampler, column thermostat and diode array detector. K.F.: 10.10%; MS and IR spectra were consistent with the structure.

| | Elemental analysis (%): | | | | | | |
|---|---|---|---|---|---|---|---|
| | C | H | Gd | I | N | Na | |
| Calcd. | 32.23 | 2.70 | 13.18 | 21.28 | 4.70 | 5.78 | |
| Found | 32.24 | 2.30 | 12.88 | 21.03 | 4.67 | 5.53 | anhydrous |

What is claimed is:
1. A compound of the formula (II), both in the racemic and optically active forms

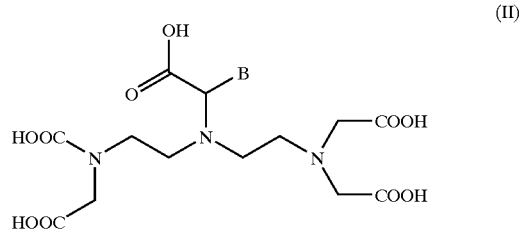

(II)

in which B is selected from the group consisting of:

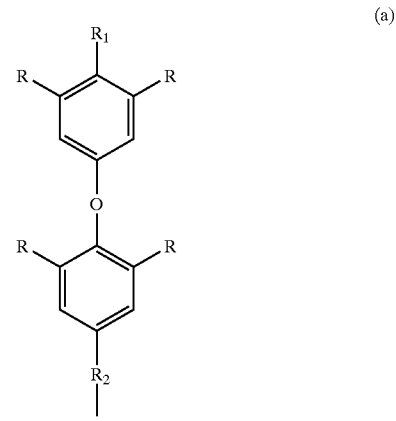

(a)

wherein:
R=independently H, halogen,
$R_1$=H, —OH, —N(R'$_1$)$_2$, —COOR'$_1$, —CON(R'$_1$)$_2$,
$R_2$=$C_1$–$C_6$ linear or branched alkyl, optionally substituted with —OH, —COOR'$_2$— groups and/or interrupted by —CON(R'$_2$)— groups,
R'$_1$=independently H or $C_1$–$C_6$ linear or branched alkyl, optionally substituted with 1 to 5 —OH groups, R'$_2$=independently H or C$_1$–C$_6$ linear or branched alkyl, optionally substituted with 1 to 5 —OH groups, or

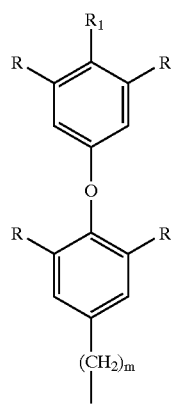

(b)

wherein:

R=independently H, Br, I,

R$_1$=OH, N(R'$_1$)$_2$, COOR'$_1$, —CON(R'$_1$)$_2$, m=integer 1–6;

R'$_1$=independently H or C$_1$–C$_6$ linear or branched alkyl optionally substituted with 1 to 5 —OH groups;

and complexes of said compound with bi- or trivalent metal ions.

2. The compound according to claim 1, wherein B is selected from the group consisting of:

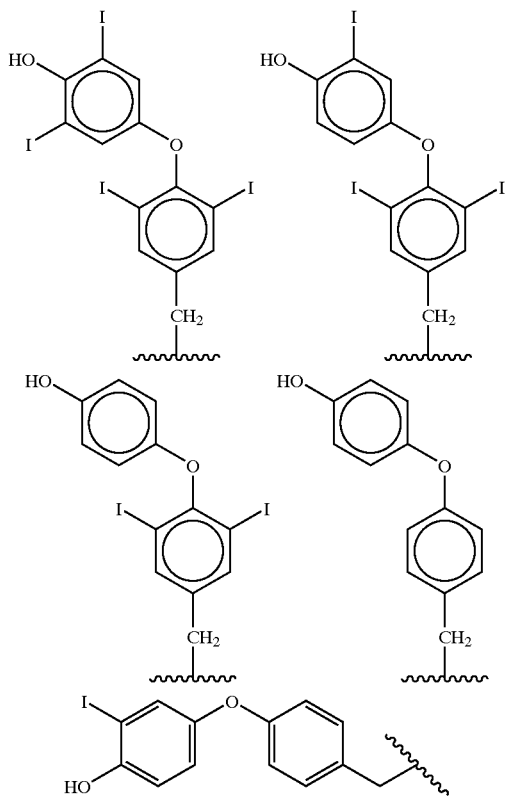

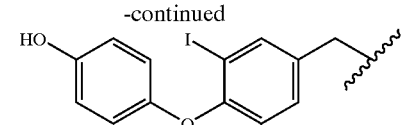
-continued

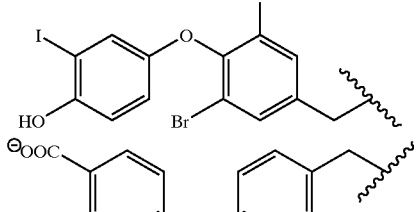

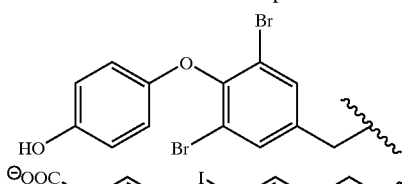

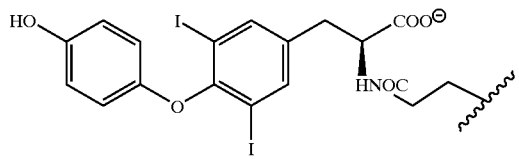

3. The compound as claimed in claim 1 or 2, in the form of a complex with metal ions of atomic number from 20 to 31,39, from 42 to 44,49 and from 57 to 83 and the salts thereof with physiologically acceptable organic bases selected from primary, secondary or tertiary amines, or basic amino acids, or with inorganic bases the cations of which are sodium, potassium, magnesium, calcium or the mixtures thereof.

4. A compound as claimed in claim 3, wherein the complexed bi- or trivalent metal ion is selected from the group consisting of Fe$^{(2+)}$, Fe$^{(3+)}$, Cu$^{(2+)}$, Cr$^{(3+)}$, Gd$^{3+}$, Eu$^{(3+)}$, Dy$^{(3+)}$, La$^{(3+)}$, Yb$^{(3+)}$ and Mn$^{(2+)}$.

5. A compound selected from the group consisting of:
  N,N-Bis[2-[bis(carboxymethyl)amino]ethyl]-O-(4-hydroxyphenyl)-3,5-diiodo-L-tyrosine;
  N,N-Bis[2-[bis(carboxymethyl)amino]ethyl]-O-(4-hydroxyphenyl)-L-tyrosine;
  N,N-Bis[2-(bis(carboxymethyl)amino]ethyl]-O-(3,5-diiodo-4-hydroxyphenyl)-3,5-diiodo-L-tyrosine;
  N,N-Bis[2-[bis(carboxymethyl)amino]ethyl]-O-(3-iodo-4-hydroxyphenyl)-3,5-diiodo-L-tyrosine;
  N,N-Bis[2-(bis(carboxymethyl)amino]ethyl]-O-(4-hydroxyphenyl)-3,5-diiodo-D-tyrosine;
  [[N,N-Bis[2-[bis(carboxymethyl)amino]ethyl]-O-(4-hydroxy-3-iodophenyl)-L-tyrosine;
  N,N-Bis[2-[bis(carboxymethyl)amino]ethyl]-3,5-dibromo-O-(4-hydroxy-phenyl)-L-tyrosine;
  N,N-Bis[2-[bis(carboxymethyl)amino]ethyl]-3,5-dibromo-O-(4-hydroxy-3-iodophenyl)-L-tyrosine;

N,N-Bis[2-[bis(carboxymethyl)amino]ethyl]-O-(4-carboxyphenyl)-3,5-diiodo-L-tyrosine; and N,N-Bis[2-(bis(carboxymethyl)amino]ethyl]-O-(4-carboxyphenyl)-L-tyrosine.

6. A paramagnetic chelate selected from the group consisting of:

a gadolinium complex of N,N-Bis[2-[(carboxymethyl)amino]ethyl]-O-(4-hydroxyphenil)-3,5-diiodo-L-tyrosine salified with deoxy-1-(methylamino)-D-glucitol (1:2);

a gadolinium complex of N,N-Bis[2-[(carboxymetyl)amino]ethyl]-O-(4-hydroxyphenil)-L-tyrosine salified with 1-deoxy-1-(methylamino)-D-glucitol (1:2);

a gadolinium complex of N,N-Bis[2-[bis(carboxymetyl)amino]ethyl]-O-(3,5-diiodo-4-hydroxyphenil)-3,5-diiodo-L-tyrosine salified with 1-deoxy-1-(methylamino)-D-glucitol (1:2);

a gadolinium complex of N,N-Bis[2-[bis(carboxymetyl)amino]ethyl]-O-(3-iodo-4-hydroxyphenil)-3,5-diiodo-L-tyrosine salified with 1-deoxy-1-(methylamino)-D-glucitol (1:2);

a gadolinium complex of N,N-Bis[2-[bis(carboxymetyl)amino]ethyl]-O-(4-hydroxyphenil)-3,5-diiodo-D-tyrosine salified with 1-deoxy-1-(methylamino)-D-glucitol (1:2);

a gadolinium complex of N,N-Bis[2-[bis(carboxymetyl)amino]ethyl]-O-(4-hydroxy-3-iodophenil)-L-tyrosine salified with 1-deoxy-1-(methylamino)-D-glucitol (1:2);

a gadolinium complex of N,N-Bis[2-[bis(carboxymetyl)amino]ethyl]3,5-dibromo-O-(4-hydroxyphenil)-L-tyrosine salified with 1-deoxy-1-(methylamino)-D-glucitol (1:2);

a gadolinium complex of N,N-Bis[2-[bis(carboxymetyl)amino]ethyl]3,5-dibromo-O-(4-hydxoxy-3-iodophenil)-L-tyrosine salified with 1-deoxy-1-(methylamino)-D-glucitol (1:2);

a gadolinium complex of N,N-bis[2-[bis(carboxymetyl)amino]ethyl]-O-(4-carboxphenil)-3,5-diiodo-L-tyrosine salified with 1-deoxy-1-(methylamino)-D-glucitol (1:3);

a gadolinium complex of N,N-Bis[2-[bis(carboxymetyl)amino]ethyl]-O-(4-carboxyphenil)-L-tyrosine salified with 1-deoxy-1-(methylamino)-D-glucitol (1:3);

and a gadolinium complex of (S)-N-[4-[Bis[2-[bis(carboxymethyl)amino]ethyl)amino]-4-carboxy-1-oxobutyl]-O-(4-hydroxyphenyl)-3,5-diiodo-L-tyrosine tri-sodium salt.

7. A contrast diagnostic pharmaceutical composition for magnetic resonance imaging comprising at least one complex chelate as claimed in claim 1 or a physiologically acceptable salt thereof.

8. A method of magnetic resonance imaging the blood pool district of human or animal body comprising administering to said human or animal an effective imaging amount of the contrast diagnostic pharmaceutical composition of claim 7, and then magnetic resonance imaging the human or animal body.

* * * * *